(12) United States Patent
Choi

(10) Patent No.: US 11,771,784 B2
(45) Date of Patent: Oct. 3, 2023

(54) MATERIAL, DEVICE, AND METHOD FOR DEACTIVATING PATHOGEN IN AEROSOL, AND METHODS FOR MANUFACTURING THEREOF

(71) Applicant: Hyo-Jick Choi, Edmonton (CA)

(72) Inventor: Hyo-Jick Choi, Edmonton (CA)

( * ) Notice: Subject to any disclaimer, the term of this patent is extended or adjusted under 35 U.S.C. 154(b) by 1070 days.

(21) Appl. No.: 16/326,187

(22) PCT Filed: Aug. 18, 2017

(86) PCT No.: PCT/IB2017/001143
§ 371 (c)(1),
(2) Date: Feb. 15, 2019

(87) PCT Pub. No.: WO2018/033793
PCT Pub. Date: Feb. 22, 2018

(65) Prior Publication Data
US 2020/0179547 A1     Jun. 11, 2020

Related U.S. Application Data

(60) Provisional application No. 62/377,209, filed on Aug. 19, 2016.

(51) Int. Cl.
*B01D 46/00* (2022.01)
*A61L 2/232* (2006.01)
(Continued)

(52) U.S. Cl.
CPC .......... *A61L 2/232* (2013.01); *A41D 13/1192* (2013.01); *A61L 9/16* (2013.01);
(Continued)

(58) Field of Classification Search
CPC ...... B01D 46/0028; B01D 27/00; A61L 2/232
See application file for complete search history.

(56) References Cited

U.S. PATENT DOCUMENTS

| 7,044,993 | B1 * | 5/2006 | Bolduc | B01D 39/1623 261/107 |
| 2009/0075231 | A1 * | 3/2009 | Tontz | A61C 17/02 433/88 |
| 2015/0313912 | A1 * | 11/2015 | Karandikar | A61K 9/7007 514/184 |

FOREIGN PATENT DOCUMENTS

| CN | 101716359 A | 6/2010 |
| CN | 101720254 A | 6/2010 |
| (Continued) |

OTHER PUBLICATIONS

Tessier et al., "Antimicrobial Fabrics Coated with Nano-Sized Silver Salt Crystals", 2005, NSTI-Nanotech vol. 1 pp. 762-764 (Year: 2005).*

(Continued)

*Primary Examiner* — Robert A Hopkins
(74) *Attorney, Agent, or Firm* — PV IP PC; Ude Lu; Xing Lu

(57) ABSTRACT

A pathogen-deactivating fibrous material is coated with salt crystals or salt crystal layer. The salt crystals or coating on the supporting fibrous material layer dissolves upon exposure to pathogenic aerosols and recrystallizes during evaporation of water from the pathogenic aerosols. Recrystallization of the salt deactivates pathogens. The pathogen-deactivating fibrous material can be used in a sanitizing fabric, an air filtering device, such as respiratory devices, masks, furnace filter devices, air conditioning device, vehicle cabin filter device, etc., and can provide a universal personal protection for preventing infections.

14 Claims, 18 Drawing Sheets

(51) Int. Cl.
*A41D 13/11* (2006.01)
*A61L 9/16* (2006.01)

(52) U.S. Cl.
CPC ...... *B01D 46/0028* (2013.01); *A61L 2209/14* (2013.01); *A61L 2209/16* (2013.01); *A61L 2209/21* (2013.01); *B01D 2279/50* (2013.01); *B01D 2279/65* (2013.01)

(56) References Cited

FOREIGN PATENT DOCUMENTS

| | | |
|---|---|---|
| CN | 103952907 A | 7/2014 |
| CN | 203802981 U | 9/2014 |
| JP | 2002-085056 | 3/2002 |
| WO | 2007120509 A2 | 10/2007 |
| WO | 2008009651 A1 | 1/2008 |
| WO | 2014151836 A1 | 9/2014 |

OTHER PUBLICATIONS

Quan, F.-S. et al.: "Universal and reusable virus deactivation system for respiratory protection", Scientific Reports, Vo. 7, article No. 39956, 10 pages, Jan. 4, 2017.

Choi, H.-J. et al.: "Stability of influenza vaccine coated onto microneedles", Biomaterials, Vo. 33, pp. 3756-3769, 2012.

Choi, H.-J. et al.: "Stability of whole inactivated influenza virus vaccine during coating onto metal microneedles", Journal of Controlled Release, vol. 166, pp. 159-171, 2013.

Choi, H.-J. et al.: "Effect of Osmotic Pressure on the Stability of Whole Inactivated Influenza Vaccine for Coating on Microneedles", PLOSOne, vol. 10(7), article No. e0134431, 22 pages, 2015.

PCT/IB2017/001143 International Search Report, 4 pages, dated Jan. 3, 2018.

PCT/IB2017/001143 Written Opinion of the International Search Authority, 5 pages, dated Jan. 3, 2018.

\* cited by examiner

*Fig. 12*

[Graph 1200: Body Weight Change (%) vs Time (Day), with legend: CA/09 stock, Aerosol, Filter_bare, Filter_wet, Filter_wet+600μL, Filter_wet+1200μL]

*Fig. 13*

[Graph 1300: Survival Rate (%) vs Time (Day), with legend: CA/09 stock, Aerosol, Filter_bare, Filter_wet, Filter_wet+600μL, Filter_wet+1200μL]

- ● CA/09 stock
- ■ Filter$_{wet+600\mu L}$ : ambient condition
- □ Filter$_{wet+600\mu L}$ : 1-day incubation at 37°C, 70% RH

*Fig. 25*

- 2502: Coating a supporting member with a salt-coating formulation to obtain a coated supporting member
- 2504: Drying the coated supporting member to obtain a dried filter that is coated with salt crystals
- 2506: Installing the dried filter in an air filter device

*Fig. 26*

A — Filter

B

C — Coating fomulation

D — Spray nozzle, Salt formulation droplets, Filter

E — Coating formulation

F

G — Filter support / Filter — Front view; Filter support — Top view

H — Salt-coated Filter

2600

MATERIAL, DEVICE, AND METHOD FOR DEACTIVATING PATHOGEN IN AEROSOL, AND METHODS FOR MANUFACTURING THEREOF

FIELD

Embodiments disclosed herein relate generally to devices and methods for filtration of and deactivating airborne pathogen. The embodiments disclosed herein include pathogen deactivating materials, a filter for deactivating pathogen, a method for manufacturing the pathogen deactivating materials for the filter, and method for deactivating an airborne pathogen (e.g., pathogenic aerosol).

BACKGROUND

Air Filter:

Generally, controlling transmission of respiratory diseases can be attempted by using an air filter, such as for example a respirator or a mask. Known air filters generally capture airborne particulates based on the size of the airborne particulates (e.g., virus, bacteria, fungi, etc.), to attempt prevention or reduction of the spread of air-transmissible diseases. For example, N95 respirators were used to reduce infection risk associated with severe acute respiratory syndrome (SARS) virus. However, an air filter may not provide satisfactory and sufficient protection against some airborne pathogens. There are many factors affecting the efficacy of an air filter. The air filter may not adequately filter some small size of airborne pathogens, providing ineffective protection against these airborne pathogens. For example, National Institute for Occupational Safety and Health (NIOSH)-certified N95 respirators cannot provide an expected level of protection against 40-50 nm infectious particles including aerosols. It is to be understood that the efficacy of the air filter, for example, a respirator or mask, also depends on how well leakage of pathogens through the air filter is minimized. Even if the air filter has a minor leakage for a small portion of airborne pathogens, this still could cause failure in preventing an individual from infection, which in turn may cause the spread of airborne infectious disease. Thus, use of an air filter, for example, an N95 respirator, requires trained personnel to conduct a time-consuming fit test. This would thwart the public use of an air filter during, for example, a pandemic. Furthermore, contamination/transmission (i.e., one or more of cross contamination, cross transmission, contact contamination, and contact transmission) may be of a safety concern due to residual pathogens such as a virus, bacteria, fungi, etc. retained in the air filter, for example, respirator or facial/surgical mask, after use. Moreover, a used air filter usually cannot be reused because of damages due to re-sterilization. For example, an N95 respirator is recommended for a single use only. As a result, an estimated cost of air filters, for example, respirators or masks, in one pandemic outbreak could reach up to $10 billion in U.S. alone.

Sanitizing Device:

Contamination by hand contact represents a major route of infection and transmission of infectious bacteria, threatening the safety of mothers, newborns, children, and elderly in private and public places. Gram negative and gram positive bacteria can survive for few days to many months on diverse surfaces. Most of the recommendations by WHO have been based on the disinfection of hands by practicing proper hand hygiene techniques (i.e. handwashing with soap and clean water or alcohol-based hand sanitizers) for the control of pathogens. However, in low-resource countries, limited supplies and poor adherence to recommended hand hygiene practices resulted in an increased incidence of primary/secondary infections. Therefore, development of a simple but efficient antiseptic device has been considered as a key non-pharmaceutical intervention technology in preventing the spread of infectious diseases.

To this end, it is aimed to develop a reusable antibacterial cloth with high compliance to decontaminate hands without using traditional liquid-based antiseptic agents. Unfortunately, all conventional antibacterial methods utilize halogens (e.g., N-halamines), metals (e.g., silver nitrate, silver-copper), quaternary ammonium compounds, and antibody-antigen reaction, which have restricted their commercial application due to drawbacks of each method, such as slow inactivation (inactivation should be rapid in the order of minutes, not hours) or binding-specificity. These factors make them impractical and expensive to use on a large scale. Based on the above observations, we identified the critical parameters in developing pathogen-inactivating filters to be: rapid/effective inactivation, strain-nonspecificity, reusability, and simple production with low cost.

SUMMARY OF INVENTION

Embodiments disclosed herein are directed towards addressing the above problems and disadvantages associated with the generally known air filter and sanitizing fabric devices. Embodiments disclosed herein relate generally to filtration of a pathogen, deactivation of the pathogen, or both filtration and deactivation of the pathogen. Specifically, the embodiments disclosed herein relate to a filter material, an air filter, method for manufacturing the filter material, method for manufacturing the air filter, and method for filtering an airborne pathogen. More specifically, the embodiments disclosed herein relate to a pathogen-deactivating air filter, method for manufacturing the pathogen-deactivating air filter, and method for deactivating a pathogenic aerosol. Some other embodiments disclosed herein relate to sanitizing fabric devices, and method for manufacturing the sanitizing fabric devices.

In a broad aspect, the embodiments herein provide a pathogen-deactivating air filter and/or sanitizing fabric device that includes a salt crystal layer coated on a supporting member (e.g., fibrous material, fibrous layer, fabric, porous membrane, mesh, etc.). The embodiments disclosed herein utilize salt recrystallization disposed on the supporting member for evaporating water from an aerosol to deactivate pathogens contained therein. The evaporation of water by the salt recrystallization process causes physical damage, chemical damage, or both physical and chemical damages to the pathogen.

Some of the embodiments disclosed herein are directed towards air filters that are easy to use, that are reusable without reprocessing, are recyclable, and also are capable of deactivating a broad range of pathogenic aerosols (i.e., pathogens in the aerosol). Thus, the embodiments disclosed herein are effective at reducing the risk of contamination/transmission of pathogens. The pathogen-deactivating air filter material can be used alone or in combination with another air filter material. In an aspect, the pathogen-deactivating air filter material can be incorporated into an air filter device (e.g., filter mask, furnace filter, air conditioner filter, vehicle cabin filter, etc.) or an air purifier device.

In yet another broad aspect, the embodiments disclosed herein provide methods for manufacturing a pathogen-deactivating material. In an aspect, the pathogen-deactivating material includes a salt crystal layer obtained with a material in a salt-coating solution. In an aspect, the salt-coating solution contains an organic or inorganic salt. In an aspect, the salt-coating solution further contains a surfactant. In an aspect, the salt-coating solution further contains an additive. In an aspect, the salt-coating solution further contains an excipient. In an aspect, the salt-coating solution does not contain any surfactant.

In another broad aspect, the embodiments disclosed herein provide methods for deactivating a pathogenic aerosol. For example, the method includes absorbing the pathogenic aerosol to a salt crystal layer of the pathogen-deactivating material, dissolving the salt crystal in contact with the pathogenic aerosol, and then recrystallizing the salt dissolved therein. Deactivation or destruction of the pathogen can be credited to the recrystallization of the salt, and increased electrostatic interaction and osmotic pressure.

BRIEF DESCRIPTION OF THE DRAWINGS

References are made to the accompanying drawings that form a part of this disclosure, and which illustrate embodiments in which the apparatus and methods described in this specification can be practiced. Like reference numbers represent like parts throughout the drawings.

FIG. 12 shows body weight change data of mice after being infected with penetration dosage of the virus on pathogen-deactivating filters relative to post infection time, according to some embodiments.

FIG. 13 shows survival rates of mice after being infected with a penetration dosage of the virus on pathogen-deactivating filters relative to post infection time, according to some embodiments.

FIG. 14 shows lung virus titer data of mice at day 4 following infection with penetration dosages of the virus on pathogen-deactivating filters, according to some embodiments.

FIG. 15 shows lung inflammatory cytokine interferon-γ (IFN-γ) level in the mice after being infected penetration dosage of the virus on pathogen-deactivating filters, according to some embodiments.

FIG. 20 shows lung virus titer data of mice infected with CA/09 virus before and after being incubated on the salt-crystal coated filters for 60 minutes.

FIG. 21 shows body weight change data of mice infected with penetration dosage of the virus on pathogen-deactivating filters relative post infection time, according to some embodiments.

FIG. 22 shows virus titer data of aerosolized CA/09 H1N1, PR/34 H1N1, and VN/04 H5N1 viruses incubated on pathogen-deactivating filters, according to some embodiments.

FIG. 23 shows body weight change data of mice infected with penetration dosages of CA/09 virus on a pathogen-deactivating filter before and after exposure to 37° C. and 70% RH for 1 day relative to post infection time, according to an embodiment.

FIG. 24 shows a survival rate data of the mice infected with penetration dosages of CA/09 virus on a pathogen-deactivating filter before and after exposure to 37° C. and 70% RH for 1 day relative to post infection time, according to an embodiment.

FIG. 25 shows a flowchart of an embodiment of a method for manufacturing a pathogen-deactivating filter material and a multiple-layered structure.

FIG. 26 shows a flowchart of an embodiment of a method for manufacturing a pathogen-deactivating filter material.

DETAILED DESCRIPTION

Figure 1A:
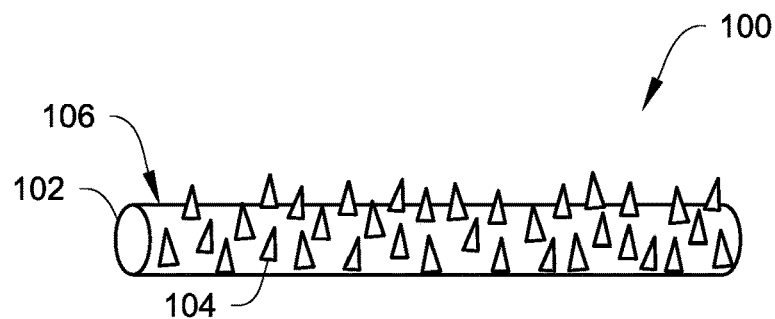
FIGS. 1A-1D show schematic drawings of a fiber material for deactivating a pathogenic aerosol according to an embodiment.

Respiratory infections are one of the leading causes of acute illness in the United States. Respiratory infections can be transmitted via inhalation of pathogenic aerosols. Further, respiratory infections can be spread to the public via exhalation of pathogenic aerosols by one who is infected. The pathogenic aerosols are also known as infectious aerosols. The pathogenic aerosols are aerosolized pathogen particles. In some embodiments, the pathogenic aerosols can be airborne water droplets containing transmissible pathogens. The pathogenic aerosols can be originated from, for examples, breathing, coughing, sneezing, talking, or the like. The transmissible pathogens can include but not limited to measles, influenza virus, adenovirus, African swine fever virus, Varicella-Zoster virus, variola virus, anthrax, respiratory syncytial virus, *Escherichia coli, Klebsiella pneumoniae, Francisella tularensis, Yersinia pestis* bacilli, *Mycobacterium tuberculosis*, etc. In some embodiments, the transmissible pathogens are respiratory pathogens.

Environmental factors such as temperature, humidity, radiation, and ozone have been found closely related to the stability of a virus. It is generally understood that aerosolized influenza virus can survive 1 to 36 hours in an airborne state. For example, the deactivation rates ($\alpha = -(\ln N_t - \ln N_0)/t$) for avian influenza viruses in aerosols are reported to be in the $10^0$-$10^2$ day$^{-1}$ range; while the deactivation rates for the avian influenza viruses in cool water with low salinity are reported to be in the $10^{-1}$-$10^{-2}$ day$^{-1}$ range. However, due to many environmental factors which can affect the deactivation rates, reported data is hard to generalize, and thus there can be many exceptions to these ranges of deactivation rates. For example, on bank notes that have a presence of mucus, influenza A/Moscow/10/99 (H3N2) can survive up to 17 days. However, despite its longevity in mucus, it can be assumed that transmission through the aerosols is the most important route for influenza virus. Aerosols can achieve superior target site penetration with an infectious dose of 50 percent ($ID_{50}$) (0.6–3.0 tissue culture infectious dose of 50 percent ($TCID_{50}$)). Additionally, virions corresponding to 0.67 $TCID_{50}$ can be placed into one aerosol droplet. Therefore, it is clear that aerosol plays an important role in the airborne transmission of, for example, influenza.

Clinical symptoms associated with common respiratory infections caused by respiratory pathogens include, but are not necessarily limited to, bronchiolitis (respiratory syncytial virus), bronchopneumonia (influenza viruses, respiratory syncytial virus, adenoviruses), coryza (rhinoviruses, coronaviruses), and croup (parainfluenza viruses), influenza (influenza viruses), smallpox (variola virus), etc. Respiratory pathogens may cause highly similar clinical symptoms, and as a result, some respiratory pathogens may be indistinguishable from one another based on symptoms alone. Respiratory infections can lead to epidemics/pandemics. Influenza is one of the major respiratory diseases with high morbidity and mortality. An influenza pandemic normally occurs when a new strain of influenza virus, for example, influenza A virus, emerges due to antigenic shift. There were three major deadly influenza outbreaks in the 20th century: H1N1 subtype in 1918, H2N2 subtype in 1957, and H3N2 subtype in 1968. All of these outbreaks were highly contagious and caused over 50 million deaths. Recently, there was an outbreak of H5N1 avian influenza in the Southeast Asia, which results in the death of more than 150 million birds. The H5N1 avian influenza can also affect the human being and, in some cases, cause mortality to the human being. From 2003 to 2011, 306 deaths were reported out of 519 human infections, amounting to 59% mortality rate. The avian flu strain H5N1 has been zoonotic so far. That is, human infections are only associated with direct contact with an infected poultry, and it does not spread from person to person. However, a human-adapted avian influenza virus might emerge, which would trigger devastating worldwide pandemics and cause great economic toll. Based on the similarities between the H1N1 subtype and the H5N1 avian influenza strain, an H5N1 influenza pandemic is expected to cause 1.7 million deaths in the United States and 180-360 million deaths worldwide. For moderate pandemics, like the ones in 1957 and 1968, the health costs alone have been estimated to approach $181 billion.

Further, respiratory pathogens can be used as a biological weapon. For examples, smallpox, which is a highly infectious and deadly disease caused by the airborne variola virus, can be used as a biological weapon due to its capability to affect large populations. Smallpox can be transmitted either through breathing aerosols that are exhaled/coughed out by an infected person or through direct skin contact. Due to its high mortality (about 30%) and contagion, smallpox is considered extremely dangerous to public health.

Although vaccines can greatly reduce morbidity and mortality in some respiratory infections, a major disadvantage is that new vaccines may need to be constantly developed to maintain their efficacy because of the shifts and drifts of antigens. Further, a vaccine can be made only after the new strain has been identified. Thus, vaccines may not be available until, at the earliest, 6 months after the initial outbreak of a pandemic. Even if an effective viral vaccine was developed, there were still many potential problems such as the limited supply of vaccines due to for example insufficient production capacity and/or time-consuming manufacturing process. Accordingly, in the absence of effective vaccines, air filters such as respirators and masks worn over the nose and mouth can be alternative means for controlling and preventing respiratory infections. For example, N95 respirators were reported to reduce the risk of infections from severe acute respiratory syndrome (SARS) virus effectively. An effective way to control respiratory infections in lieu of vaccination is generally by using an air filter device such as respirators or masks.

However, known air filter devices have significant drawbacks. Some known air filter devices cannot provide sufficient protection against very small sized infectious aerosols. That is, when the particulate or aerosol size is very small, filter devices are not effective in preventing the passing of the particulate or aerosol through the filter material. For example, the NIOSH-certified N95 respirator cannot protect a wearer against 40-50 nm of infectious aerosols. The efficacies of known air filter devices depend on the mesh size of the air filter material, which sets up a threshold limit for the infectious aerosols. That is, the infectious aerosols are removed from breathed air only when their sizes are above this threshold limit. On the other hand, the infectious aerosols can be inhaled into wearer's lung (of exhaled to the public) when their sizes are below this threshold limit.

The efficacies of known air filter devices also depend on the seal of the air filter. An insufficient seal can lead to a leakage through the known air filter device. A leak in the known air filter devices cannot provide complete protection against respiratory infections. Thus, the known air filter devices, such as respirators or masks, may need trained personnel to carry out time-consuming fit tests for wearers. However, the time-consuming fit test makes the known air filter devices, for example, N95 respirators, an impractical measure during a pandemic. In addition, it is not practical for young children, seniors, and patients having a chronic lung disease to wear a respirator for a long period, as the respirator may make breathing difficult and cause chest pain. Further, with known air filter devices, there is also a safety concern about secondary infection due to pathogens on a used air filter. Further, it is impossible to re-sterilize the used known air filter devices without damaging the filter material of the known air filter devices. Thus, the known air filter materials and devices are generally recommended for single use only and are generally required to be disposed of as biohazard materials. As a result, estimated cost in one pandemic outbreak could range up to $10 billion in U.S. alone.

Due to these factors, the use of air filter devices, for example, N95 respirators, on a large scale is impractical and expensive during an epidemic or pandemic. Past experiences in severe acute respiratory syndrome (SARS), H1N1 swine flu, and Middle East respiratory syndrome (MERS) indicate that surgical masks have been most widely adopted by the public, despite these surgical masks not having any proof that they provide any real protection against infectious aerosols. Thus, individuals and health workers are disadvantaged due to lack of effective personal protective measures during the outbreak, in particular at the early stage with no effective vaccine available.

Disclosed herein are materials and devices for overcoming the shortcomings of the known surgical masks, respirators, and other known air filter devices described above. For example, a filter material which can be used in air filter devices is configured to deactivate a pathogenic aerosol. In an embodiment, the filter material is manufactured by modifying fibers or a surface of a fabric with salt crystals having a continuous or discontinuous salt-coating layer. In an embodiment, salt crystals can include but not limited to nano-, micro-, macro-sized salt particles. The fibers or surface with salt crystals provides a functionalized material which inactivates pathogenic aerosol via two successive processes:

i) the salt dissolves upon exposure to the pathogenic aerosols, and ii) the salt recrystallizes as aerosols evaporate.

The recrystallization of the salt after the water has evaporated causes the pathogen to be deactivated through denaturation of antigens and/or destruction of lipid envelopes. Also, electrostatic interaction between dissolved salt ions and pathogen, and osmotic stress increase can reduce pathogenic infectivity even before crystal growth. Consequently, the increasingly higher concentrations of salt and the salt recrystallization during evaporation can cause the pathogens adsorbed to the functionalized surface physical, chemical, or physical and chemical damage. The damage, thereby, deactivates the pathogens.

In another embodiment, disclosed materials and devices can be used for developing sanitizing fabric products, including a hand sanitizing device, decontamination garments, antibacterial wipes, gowns, apron, boots, and gloves for personal infection control measures. This can eliminate infection and transmission due to the pathogenic aerosols settled and deposited on the diverse surfaces (i.e. skin, fabric, metal, paper, plastics, woods, ceramics, etc.)

The salt crystals can be coated, grown, glued, mixed, blended, and arrayed on fibers or one or more surface(s) of filter material(s). Accordingly, air filter devices that include these materials can be extremely effective in deactivating pathogenic aerosols. The salt crystals can be disposed on fibers or a layer of natural fibers, natural fabrics, synthetic fibers, synthetic fabrics, feathers, respirator masks, etc.

The embodiments disclosed herein solve the problems of generally known masks in combating pathogenic aerosols, and also provide universal means for deactivating a broad spectrum of pathogens, effectively preventing airborne pathogen transmissions. The embodiments disclosed herein are more effective against airborne pathogens, easier to use, recyclable without reprocessing, and can reduce the potential risks of contamination/transmission.

The advantages of the embodiments disclosed herein become more readily apparent upon reference to the following description and drawings. References are made to the accompanying drawings that form a part hereof, and which is shown by way of illustration of the embodiments in which the filter and the methods described herein may be practiced.

FIG. 1A shows a schematic drawing of an embodiment of pathogen-deactivating fibrous material 100 which deactivates a pathogenic aerosol. Herein, the pathogen-deactivating fibrous material 100 is also referred to as pathogen-deactivating air filter, active filtration layer, salt-crystal coated filter, salt-crystal coated fabric or salt-crystal coated air filter. The pathogen-deactivating fibrous material 100 includes a supporting material, which in this case is a fiber material 102 (synthetic or natural), wherein salt crystals 104 are disposed of thereon, i.e. its outer surface 106. The salt crystals 104 cover a substantial portion of the outer surface 106 of the fiber material 102. It is also possible that the salt crystals 104, or some of them, can be impregnated into the fiber material 102. The salt crystals 104 can include, but not limited to, inorganic salt crystals, organic salt crystals, and a mixture thereof. Accordingly, the salt crystals 104 can include a mixture of two or more different types of inorganic salts, a mixture of two or more different types of organic salts, or a mixture of both organic and inorganic salts. For example, the following salts can form the salt crystals 104: sodium chloride, potassium chloride, potassium chloride, potassium sulfate, ammonium sulfate, monosodium glutamate, sodium tartrate, potassium tartrate, magnesium phosphate, magnesium glutamate, and combinations thereof. Accordingly, the salt crystals 104 can include one or more of sodium, potassium, chloride, magnesium, sulfate, ammonium, phosphate, glutamate, tartrate, and their ions. In an embodiment, the salt crystals 104 contain only inorganic salt crystals (does not include any organic salts). In an embodiment, the salt crystals 104 contain only organic salt crystals (does not include any inorganic salts). In an embodiment, salt crystals 104 contain both inorganic and organic salt crystals. Salts collect moisture from the air above their critical relative humidity (RH) at environmental conditions. In an embodiment, moisture stability of the salt coating can be varied depending on the salt type and its composition to develop environmental condition-specific salt-coated filters. For example, critical relative humidity (RH) of sodium chloride, ammonium sulfate, potassium chloride, and potassium sulfate, is 75%, 80%, 84%, and 96%, respectively. In an embodiment, salts with high critical RH are preferred in humid environments. In an embodiment, salt crystals are of nano, micro, and macro scale.

Figure 1B:
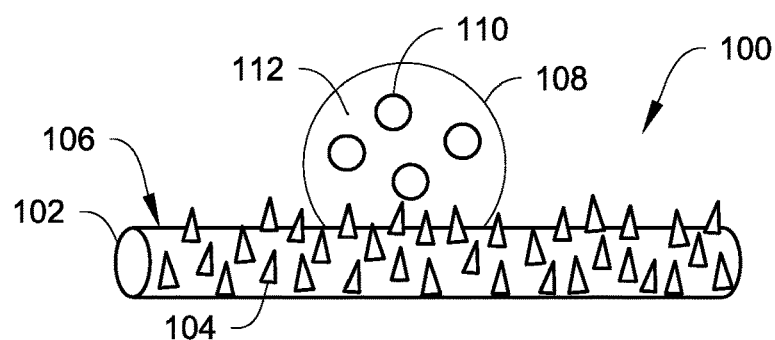

FIG. 1B shows the schematic drawing of the pathogen-deactivating fibrous material 100 of FIG. 1A with a pathogenic aerosol 108 adsorbed onto the outer surface 106. The salt crystals 104 are exposed to the pathogenic aerosol 108, which is made of pathogens 110 (e.g., virus, bacteria, fungi, etc.) surrounded by water 112.

Figure 1C:
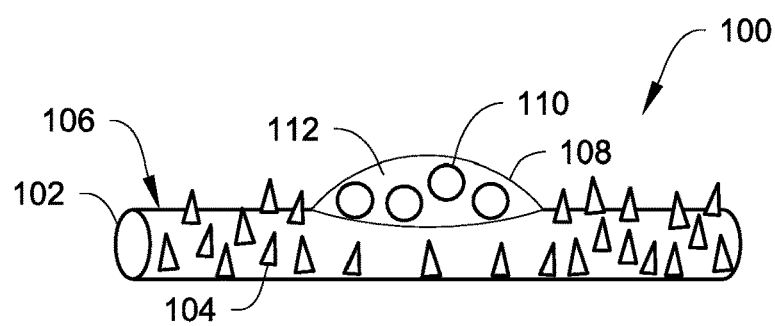

Referring to FIG. 1C, the salt crystals 104 that are in contact with the pathogenic aerosol 108 begins to dissolve, which in turn increases electrostatic interaction and osmotic pressure to the pathogens 110 in the pathogenic aerosol 108. As the size of the pathogenic aerosol 108 decreases over time due to evaporation of the water 112, the salt concentration in the pathogenic aerosol 108 is increased. Consequently, the pathogens 110 are exposed to increasing osmotic pressure and electrostatic interaction with salt ions, causing further infectivity loss of pathogens.

Figure 1D:
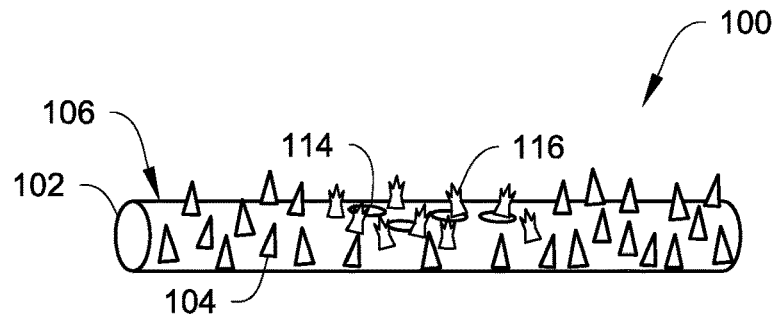

Referring to FIG. 1D, the pathogens 110 are deactivated and become deactivated pathogens 114. Further, the salts dissolved in the pathogenic aerosol 108 recrystallize to become recrystallized salt crystals 116 at the outer surface 106 when the salt concentration reaches the solubility limit. In addition to the electrostatic interaction and osmotic stress, the pathogens 110 can also be physically damaged by mechanical forces due to the formation of the recrystallized salt crystals 116. Furthermore, any surfactant, if present, in the salt crystals 104 can exert destabilization effects on the pathogens 110.

The electrostatic interaction, hyperosmotic stress, and salt recrystallization can induce both perturbations to the membrane of the pathogens 110 with irreversible deformation of the membrane and denaturation of antigenic proteins. For example, when the pathogens 110 are the virus, the electrostatic interaction, hyperosmotic stress, and the salt recrystallization process can cause damages to their envelopes and structures of surface antigens on lipid envelope, resulting in loss of infectivity. Further, the salt can also cause electrostatic potential changes to proteins, RNAs, and/or DNAs. Therefore, the deactivation of the pathogens 110 in the pathogenic aerosol 108 is caused by a robust salt crystallization process, combining the destabilizing effects of salt crystal growth with hyperosmotic pressure and electrostatic interaction.

Figure 2A:
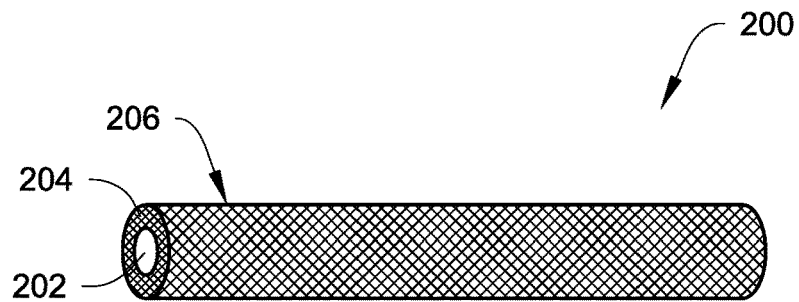
FIGS. 2A-2D show schematic drawings of a fiber material for deactivating a pathogenic aerosol according to another embodiment.

FIG. 2A shows a schematic drawing of another embodiment of pathogen-deactivating fibrous material 200 which deactivates a pathogenic aerosol. The pathogen-deactivating fibrous material 200 includes a supporting material, which in this case is a fiber material 202 (synthetic or natural), wherein a salt crystal coating layer 204 is disposed thereon, i.e., the outer surface of the fiber material 202 is completely, or substantially completely, covered by the salt crystal coating layer 204. It is also possible that the salt crystals of the salt crystal coating layer 204, or some of them, can be impregnated into the fiber material 202. The salt crystal coating layer 204 can include, but not limited to, inorganic salt crystals, organic salt crystals, and a mixture thereof. For example, the following salts can form the salt crystal coating layer 204: sodium chloride, potassium chloride, potassium chloride, potassium sulfate, ammonium sulfate, monosodium glutamate, sodium tartrate, potassium tartrate, magnesium phosphate, magnesium glutamate, and combinations thereof. Accordingly, the salt crystal coating layer 204 can include one or more of sodium, potassium, chloride, magnesium, sulfate, ammonium, phosphate, glutamate, tartrate, and their ions. In an embodiment, the salt crystal coating layer 204 contains only inorganic salt crystals (does not include any organic salts). In an embodiment, the salt crystal coating layer 204 contains only organic salt crystals (does not include any inorganic salts)). In an embodiment, salt crystal coating layer 204 contains both inorganic and organic salt crystals.

Figure 2B:
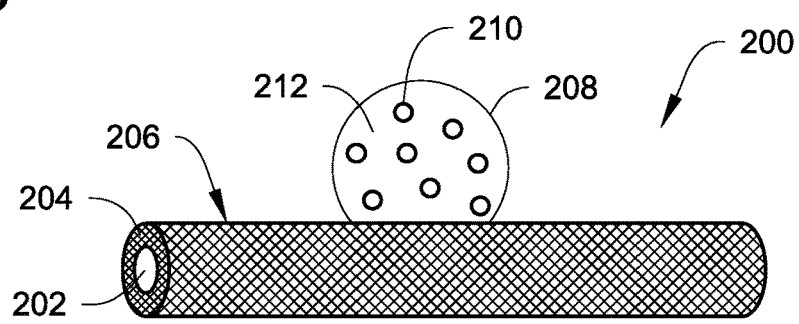

FIG. 2B shows the schematic drawing of the pathogen-deactivating fibrous material 200 of FIG. 2A. An outer surface 206 of the salt crystal coating layer 204 adsorbs a pathogenic aerosol 208. The pathogenic aerosol 208 is made of pathogens 210 (e.g., virus, bacteria, fungi, etc.) surrounded by water 212. The pathogenic aerosol 208 does not come into direct contact with the fiber material 202 because the salt crystal coating layer 204 prevents such direct contact.

Figure 2C:
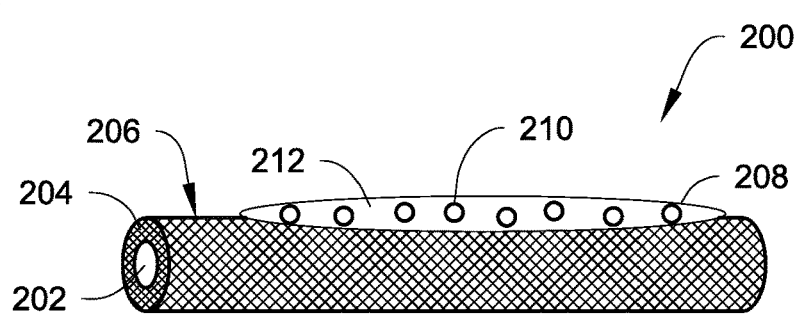

Referring to FIG. 2C, the salts from the salt crystal coating layer 204 that are in contact with the pathogenic aerosol 208 begins to dissolve, which in turn increases electrostatic interaction and osmotic stress to the pathogens 210 in the pathogenic aerosol 208. As the size of the pathogenic aerosol 208 decreases over time due to evaporation of the water 212, the salt concentration in the pathogenic aerosol 208 is increased. Consequently, the pathogens 210 are exposed to increased electrostatic interaction and osmotic pressure, causing additional infectivity loss of pathogens.

Figure 2D:
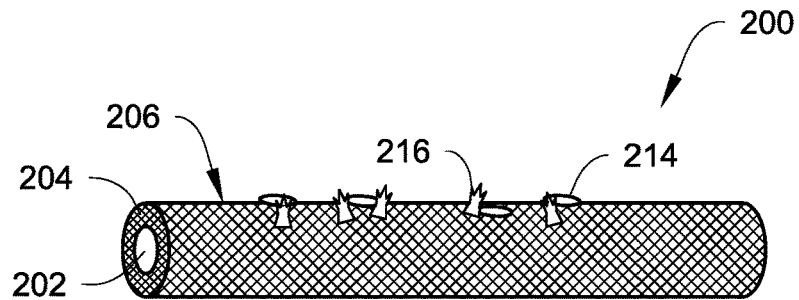

Referring to FIG. 2D, the pathogens 210 are deactivated and become deactivated pathogens 214. Further, the salts dissolved in the pathogenic aerosol 208 recrystallize 216 to reform the salt crystal coating layer 204, and the outer surface 206 is also reformed when the salt concentration reaches the solubility limit. In addition to the electrostatic interaction and osmotic stress, the pathogens 210 can also be physically damaged by mechanical forces due to the reformation of the salt crystal coating layer 204. In addition, any surfactant, if present, in the salt crystal coating layer 204 can exert destabilization effects on the pathogens 210.

The electrostatic interaction, hyperosmotic stress, and salt recrystallization can induce both perturbations to the membrane of the pathogens 210 with irreversible deformation of the membrane and denaturation of antigenic proteins. For example, when the pathogens 210 are the virus, the electrostatic interaction, hyperosmotic stress and the salt recrystallization process can cause damages to their envelopes and structures of surface antigens on lipid envelope, resulting in loss of infectivity. Further, the salt can also cause electrostatic potential changes to proteins, RNAs, and/or DNAs. Therefore, the deactivation of the pathogens 210 in the pathogenic aerosol 208 is caused by a robust salt crystallization process, combining the destabilizing effects of salt crystal growth with electrostatic interaction and hyperosmotic stress during drying of aerosols.

The salt crystal coating layer 204 and the fiber material 202 can be separable members or a joined unitary piece. In an embodiment, the salt crystal coating layer 204 is a separable component formed on the fiber material 202. The pathogen-deactivating fibrous material 200 can have more than one salt crystal layer. The pathogen-deactivating fibrous material 200 can have more than one fiber material 202.

The deactivation of pathogenic aerosol 108, 208 described above are not specific to a particular pathogen but can be used to deactivate various types of aerosolized pathogens, such as virus, bacteria, fungi, protein, biomolecules, or any combinations thereof. As the cycle of salt dissolving and crystallizing can be repeated without damaging the pathogen-deactivating fibrous material 100, 200, this material 100, 200 allows for a personal protective air filter device that is reusable.

The pathogen-deactivating fibrous material 100, 200 can be applied to a wide range of existing technologies such as masks, respirators, air filters, air purifiers, or the like to obtain low-cost and universal means for personal and public protection against airborne aerosolized pathogens. Therefore, the embodiments disclosed herein can contribute to global health by providing a more reliable means for preventing transmission and infection of pandemic or epidemic respiratory infection and bioterrorism. Further, a pathogen-deactivating filter device which includes one or more of the pathogen-deactivating fibrous material 100, 200 can be used alone or in combination with another air filter device for deactivating and optionally filtering airborne pathogens.

The pathogen-deactivating fibrous material 100, 200 can be formed from a salt-coating solution or a salt solution. The salt-coating solution is also referred to as salt-coating formulation. A composition of the salt-coating solution can include but not limited to, for example, a salt, a surfactant, an excipient, and an additive. In an embodiment, the salt-coating solution can contain at least one salt. In an embodiment, the salt-coating solution can contain at least one salt and at least one surfactant. In an embodiment, the salt-coating solution does not contain a surfactant. In an embodiment, the salt-coating solution further contains one or more excipients. In an embodiment, the salt-coating solution can further contain one or more additives to enhance such as for example, mechanical, chemical stability, adherence, dye, and/or other physical or chemical properties of the salt crystals. In an embodiment, the salt-coating solution can include one or more additives for controlling, for example, morphology and/or size of the salt crystals. In some embodiments, the salt-coating solution can contain several different kinds of additives and surfactants for desired performances.

The salt in the salt solution or salt-coating solution includes but not limited to organic salts, inorganic salts, or a combination thereof. Preferably, the inorganic salt includes those having no negative impact on human health when used in, for example, respirator or mask. More preferably, the inorganic salt crystals include but not limited to sodium chloride, potassium chloride, potassium chloride, potassium sulfate, and ammonium sulfate. In an embodiment, the inorganic salt crystal includes NaCl.

The content of a salt or a mixture of multiple salts in the composition of the salt-coating solution can be varied up to its maximum solubility limit in water. The maximum solubility limits for some salts are about 740 g/l for monosodium glutamate, about 660 g/l for (sodium/potassium) tartrates, about 360 g/l for sodium chloride, about 355 g/l for potassium chloride, about 120 g/l for potassium sulfate, about 754 g/l for ammonium sulfate.

The salt solution or salt-coating solution can include an additive. The additive can include but not limited to, for examples, polymers, metals, clay, or a combination thereof. It is to be understood that the type or kind of additive is not particularly limited if it can provide the pathogen-deactivating fibrous material 100, 200 with desired physical or chemical property. In an embodiment, a mixture of different kinds or types of additives can be used in the salt-coating solution to improve the performance of the pathogen-deactivating fibrous material 100, 200.

The salt solution or salt-coating solution can include an excipient, such as a surfactant. The excipient in the salt-coating solution may contain both salt and surfactant in water. The type and content of the excipients can be varied based on desired properties. The surfactant can improve wetting of the salt-coating solution on a hydrophobic supporting member (e.g., 102, 202). In an embodiment, the composition of the salt-coating solution requires one or more surfactants for stable salt coating, when the supporting member is hydrophobic. However, the surfactant can be an optional component in the salt-coating solution, when the supporting member is hydrophilic. In an embodiment, a mixture of different surfactants can be used in the salt-coating solution in order to achieve desired properties.

A variety of surfactants can be used in the salt-coating solution. Examples include ionic (e.g., cationic, anionic, zwitterionic) surfactants, nonionic surfactants, and biologically derived surfactants. Specific examples of surfactants can include but not limited to chemically/physically, modified/unmodified, polysorbate such as for example TWEEN™-20 and amphiphilic biomolecules (peptides, proteins).

Without limitation, the content of the surfactant can be varied from 0 to 5 v/v %. Higher concentrations of surfactant and salts are preferred to form a continuous salt coating and a thick salt coating, respectively, when the supporting member is hydrophobic. However, reduction in the content of the salt and/or the surfactant is preferred to make a discontinuous salt crystal coating when the supporting member is hydrophobic. Where the supporting member is hydrophilic, it is not necessary to have the surfactant in the salt-coating solution, but a small amount of surfactant can still be added to the salt-coating solution to enhance coating or accelerate pathogen deactivation process.

The supporting member can be hydrophobic, hydrophilic, or amphiphilic. In an embodiment, the supporting member is made of one or more of hydrophobic materials such as polypropylene, polystyrene, polycarbonate, polyethylene, polyester, polyurethane and polyamides. In an embodiment, the hydrophobic material is polypropylene (PP). In an embodiment, the supporting member is made of one or more of hydrophilic materials. In an embodiment, the supporting member can be made from a hydrophilic plant fiber. In an embodiment, the supporting member can be made from natural or synthetic fibers. In an embodiment, the supporting member can be made from one or more of feathers. The supporting member can be a porous material that allows air passing. In an embodiment, the supporting member is a porous material having a particular pore or mesh size, fiber diameter, layer thickness that can filter particulate matters. The particulate matter can include microscopic solids, liquid droplets, oil droplets, or a mixture thereof, which are suspended in air. In an embodiment, the particulate matter is an aerosol containing airborne biological agents such as for example viruses, bacteria, fungi. In an embodiment, for the fabrication of pathogen deactivation fabric, fiber diameter, the thickness of each woven or nonwoven layer, pore size, density/size of salt crystals, the thickness of salt coating, and the number of salt-coated fabric layers can be controlled to meet the specific performance requirements, such as breathability and filtration efficiency.

Conventional surgical masks and N95 respirators have a three-ply structure consisting of an inner, middle, and outer layer. The spunbond inner layer maintains contact with the face and helps support the mask, the meltblown middle layer acts as the main filtration unit, and the spunbond outer layer provides exterior structural protection. Existing suitable fiber materials include polypropylene (PP), polystyrene, polycarbonate, polyethylene, polyester, polyurethane, and polyamides. However, nonwoven fabrics made of PP fibers are used prevalently due to lower cost. In an embodiment, commercially available spunbond fabric layers with big pore diameter can be used to make salt-coated pathogen deactivation layers without using meltblown middle layer. Multiple layers of spunbond fabrics can be stacked and coated with salt as a single body. Alternatively, an individually prepared salt-coated layer can be stacked to make a multilayered structure. Salt-coated spunbond layers can be used as an active filtration layer. With increasing number of the spunbond layers and salt crystal size/salt coating thickness and filtration efficiency will increase but breathability will decrease.

In an embodiment, the supporting member can be an air filter including a conventional air filter that filters such as, for example, fogs, fumes, smokes, mists, gases, vapors, sprays, and airborne aerosols, and thereby the supporting member can remove contaminants from the air stream passing therethrough by filtration.

The shape of the supporting member is not particularly limited. In an embodiment, the supporting member can be a fiber (e.g., 102, 202) or a coating. In an embodiment, the supporting member can be a membrane.

The supporting member can be a layered structure. In an embodiment, the supporting member has only one layer. In an embodiment, the supporting member contains multiple layers.

Figure 3:
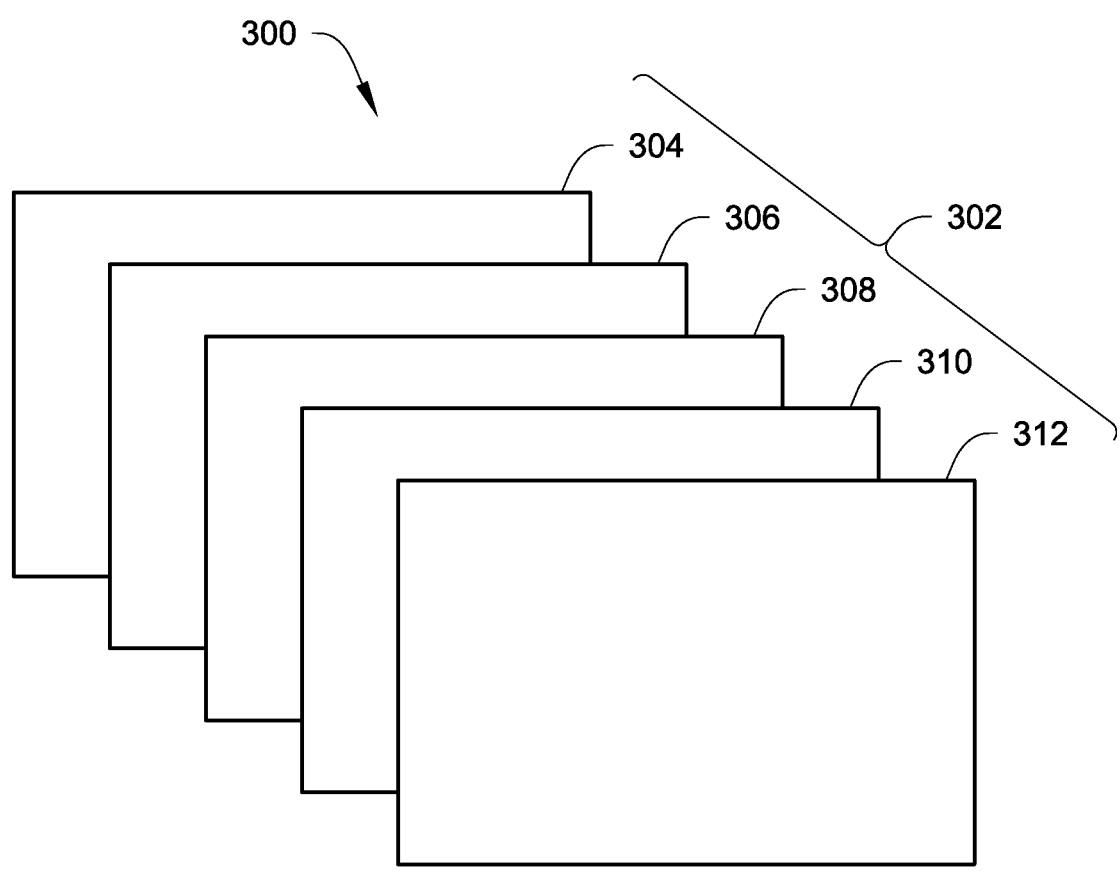
FIG. 3 shows the schematic drawing of layered materials for deactivating a pathogenic aerosol according to an embodiment.

FIG. 3 shows a multiple-layered structure 300 which includes multiple layers 302 made of, for example, layer 304, layer 306, layer 308, layer 310, and layer 312. It is to be understood that the multiple layers 302 can include more than or less than five (5) layers without any particular limitations. That is, the number of layers can be any positive integer greater than one (1), for example, 2, 3, 4, 5, 6, 7, 8, 9, 10, etc. In an embodiment, the multiple layers 302 include only two layers. In an embodiment, the multiple layers 302 include only three layers. In an embodiment, the multiple layers 302 include only four layers.

For example, the layer 308 can be the pathogen-deactivating fibrous material (e.g., 100 as shown in FIGS. 1A-1D or 200 as shown in FIGS. 2A-2D). The pathogen-deactivating fibrous material contains salt crystals or a salt-crystals coating layer. It is to be understood that any or more than one of the layers 304, 306, 308, 310, 312 can include the pathogen-deactivating fibrous material. It is to be understood that the multiple-layered structure 300 can contain multiple pathogen-deactivating fibrous materials, wherein the pathogen-deactivating fibrous materials are of the same type or a different type. It is to be understood that each layer of structure 300 can be composed of a single or multiple types of salt. It is to be understood that multiple layers in structure 300 can have the same type or different types of salt. For example, there can be a structure made of four stacked structures, e.g., three pathogen deactivating layers and one protection layer). Each of the pathogen deactivating layers can have different types of salts, (e.g., salt type A, a salt type B, and a salt type C), where each of salt types A, B, and C is one or more organic salt, one or more inorganic salt, or a combination of organic and inorganic salt.

The layers 306 and 310 each can independently be either a protective layer or an air particulate filtration layer. The protective layer is a layer that can block fluids and solid particles and protect the pathogen-deactivating fibrous material against mechanical tear and wear. The air particulate filtration layer is a layer that can filter air particulates. In an embodiment, the layer 306 is the protective layer. In an embodiment, the layer 306 is the air particulate filtration layer. In an embodiment, the layer 310 is the protective layer. In an embodiment, the layer 310 is the air particulate filtration layer. In an embodiment, the layer 308 is the pathogen-deactivating fibrous material and the layers 306 and 310 are the protective layers. In an embodiment, the layer 308 is the pathogen-deactivating fibrous material and the layers 306 and 310 are the air particulate filtration layers.

The outer layers 304 and 312 each can independently be a protective layer. Although the outer layers 304 and 312 each can also be the air particulate filtration layer or the pathogen-deactivating fibrous material, it is preferred that they are protective layers.

The material for the protective layer can be hydrophilic or hydrophobic, preferably hydrophobic. The material for the protective layer can include but not limited to synthetic fiber. In an embodiment, the material of the protective layer is polypropylene (PP) microfiber. In an embodiment, the material of the protective layer is polytetrafluoroethylene (PTFE). In an embodiment, both the outer layers 304 and 312 are hydrophobic, providing protection to the pathogen-deactivating layer. Such arrangement in which the pathogen-deactivating layer is sandwiched between two hydrophobic layers can also increase adsorption rate of pathogenic aerosols on the functionalized inner layer.

In an embodiment, the multiple-layered structure 300 has outer layers configured to prevent large contaminants or fluids and to protect the salt-functionalized or coated air filtration layer having smaller mesh size.

Without any limitation, the filter device 300 can be any air filter device including but not limited to, for example, mask, respirator, air filters, etc. The salt-coated device 300 can be any sanitizing fabric products including but not limited to, for example, a hand sanitizing device, decontamination garments, antibacterial wipes, hoods, gowns, apron, boots, and gloves, etc.

In an embodiment, the filter device 300 is a mask. In an embodiment, the filter device 300 is a surgical mask. In an embodiment, the filter device 300 is a respirator. In an embodiment, the filter device 300 is a hand sanitizing device. In an embodiment, the filter device 300 is a decontamination garment. In an embodiment, the filter device 300 is a personal protective equipment. In an embodiment, the filter device is a bio-lab air filter. In an embodiment, the filter device 300 can be a vehicle cabin air filter including car cabin air filter. In an embodiment, the filter device 300 can be a house forced air filter.

Figure 4A:
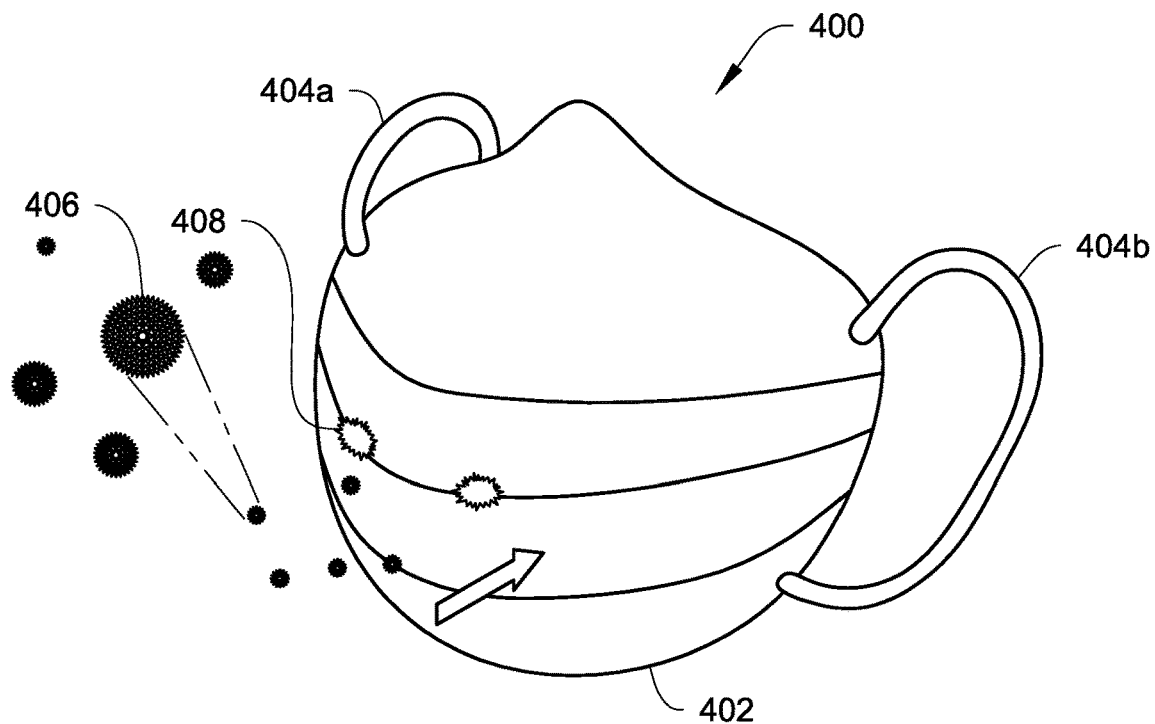
FIGS. 4A and 4B show schematic drawings of a mask for deactivating a pathogenic aerosol according to an embodiment.
Figure 4B:
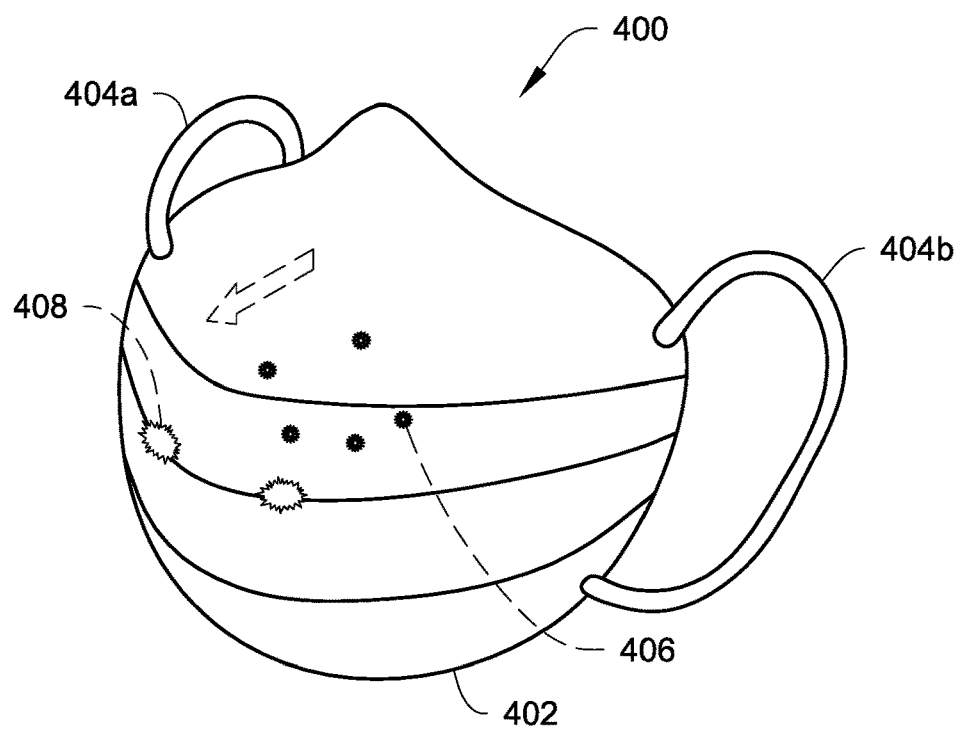

FIGS. 4A and 4B show a mask 400 having a pathogen-deactivating layer or a multiple-layered structure containing the pathogen-deactivating layer, according to an embodiment. The mask 400 includes a facemask 402 configured to cover a wearer's nose and mouth, and ear straps 404a, 404b configured to wrap around the wearer's ears to support the position of the facemask 402 when worn. In an embodiment, some masks or respirators may have additional fabric to minimize face seal leakage. In an embodiment, the additional fabric can include but not limited to nose covers, mouth covers, and/or the gaps between the inner layer of mask/respirator and face. The concept of salt-coated fibers for pathogen deactivation is not limited to the main structure of the mask/respirator but to additional parts made of fabrics used for prevention of face seal leakage as well.

FIG. 4A shows a pathogenic aerosol 406 that becomes adsorbed onto the facemask 402 via inhalation. FIG. 4B shows a pathogenic aerosol 406 that becomes adsorbed onto the facemask 402 via exhalation. As the pathogenic aerosol 406 is dried due to the recrystallization of salt crystals in the facemask 402, pathogens in the pathogenic aerosol 406 are deactivated and become deactivated pathogens 408.

The pathogenic aerosol 406 can be airborne droplets. Depending on their aerodynamic size (da) after evaporation, transmission of the airborne droplets can be classified into three modes: airborne transmission for respirable droplet nuclei with da<10 μm, droplet transmission for inhalable large droplet with 10<da<100 μm, and contact transmission for large droplets with da>100 μm. The respirable droplet nuclei and the inhalable large droplet are known to infect alveolar region and upper respiratory tract, respectively. However, since the sizes of the large droplets can decrease over time due to evaporation, airborne or droplet transmission is feasible for the large droplets. Thus, "airborne droplets" is also included in the scope of "aerosol" regardless of their physical size. In an embodiment, the pathogenic aerosol 406 can have a da from 1 nm to 200 μm. Large droplets settled and deposited on the surface can be the source of contact transmission in personal and public settings. Embodiments disclosed herein can be used to inactivate small aerosols (da<5 µm), such as a respiratory transmissible virus that is responsible for respiratory transmission, but large infectious droplets that are mainly responsible for contact transmission (e.g., bacteria on surgical mask and pathogens on any surface).

The pathogenic aerosol 406 can contain pathogens from an aqueous solution (such as aerosols), the air, or any part of the body. In an embodiment, the pathogenic aerosol 406 can contain several different pathogens. In an embodiment, the pathogenic aerosol 406 can further contain secondary components. The secondary components include but not limited to enzymes, proteins, and biomolecules such as peptides. Specific examples include but not limited to, for example, mucins, lysozyme, and lactoferrin. Without any limitation, the secondary components can also be other types of organic particles, inorganic particles or their ions, heavy metal particles or their ions, and dust. The secondary components can have widths equal to or less than the size of the pathogenic aerosol 406.

Without any limitation, a pathogen in the pathogenic aerosol 406 can include one or more of, for example, virus, bacteria, fungi, protein, and nucleotide. The virus includes but not limited to chickenpox, measles, smallpox, respiratory syncytial virus, influenza viruses, adenoviruses, rhinoviruses, coronaviruses (i.e. Middle East Respiratory Syndrome, severe acute respiratory syndrome), Ebola virus, parainfluenza viruses, variola virus, measles, African swine fever virus, and Varicella-Zoster virus.

The bacteria can include but not limited to Acute otitis media such as for example *Haemophilus influenzae, Streptococcus pneumoniae, Moraxella catarrhalis*, etc.; diphtheria such as for example *Corynebacterium diphtheria*; Legionnaires disease such as for example *Legionella pneumophila*; Pertussis such as for example *Bordetella pertussis*; Q fever such as for example *Coxiella bumetii*; Streptococcal pharyngitis; scarlet fever such as for example *Streptococcus pyogenes*; Tuberculosis such as for example *Mycobacterium tuberculosis*; Chlamydial pneumonia such as for example *Chlamydophila pneumoniae, C. psittaci, Chlamydia trachomatis; Haemophilus* pneumonia such as for example *Haemophilus* influenza; *Klebsiella pneumonia; Mycoplasma* pneumonia; Pneumococcal pneumonia such as for example *Streptococcus pneumoniae, Pseudomonas* pneumonia such as for example *Pseudomonas aeruginosa*; Anthrax such as for example *Bacillus anthracis*; methicillin-resistant *Staphylococcus aureus; Clostridium difficile*), etc.

The fungi can include but not limited to Cryptococcosis (*Cryptococcus neoformans* and *Cryptococcus gattii*), Fungal Pneumonia (*Histoplasma capsulatum, Coccidioides immitis, Blastomyces dermatitidis, Paracoccidioides brasiliensis, Sporothrix schenckii, Cryptococcus neoformans, Candida* species, *Aspergillus* species, *Mucor* species), etc.

Other examples of airborne transmissible pathogens in aerosols include without limited to *Escherichia coli, Francisella tularensis, Yersinia pestis* bacilli, nucleic acids (e.g., DNA, RNA), amino acid based biomolecules (peptide, enzyme, protein), polymer, etc.

It is to be understood that airborne transmissible pathogens can include natural mutants, mimics of amino acids or amino acid functionalities, and derivatives and variants of genetically engineered amino acid based biomolecules/organisms.

Figure 5:
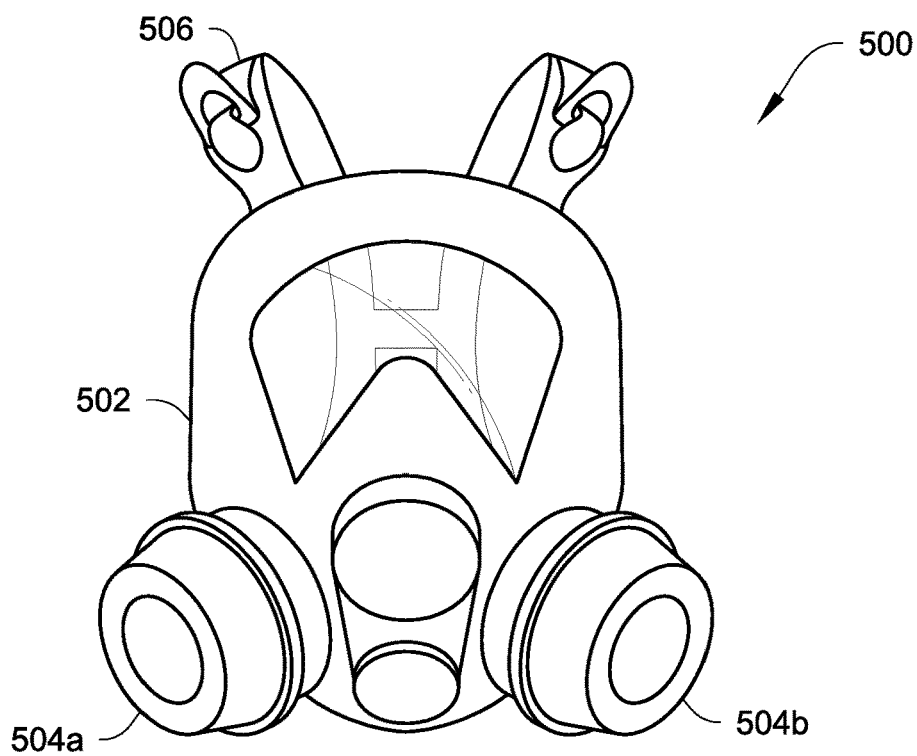
FIG. 5 shows schematic drawings of an air filter device configured to be worn by a user for deactivating a pathogenic aerosol according to an embodiment.

FIG. 5 shows an embodiment of a respirator 500 with a pathogen-deactivating fibrous material or a multiple-layered structure including the pathogen-deactivating fibrous material. The respirator 500 has a face piece 502 configured to cover a wearer's nose and mouth, two filter cartridges 504a, 504b, and a head strap 506 configured to wrap around the wearer's head to support the position of the face piece 502 when worn. The respirator 500 shown is a full-face respirator, in which the face piece 502 covers the entire face including eye, mouth, and nose. However, in another embodiment, the respirator 500 is a half-face respirator, in which the face piece 502 can cover only the bottom half of the face including wearer's nose and mouth. The half-face respirator is worn in environments where air contaminants are not toxic to the eyes. Each of the two filter cartages 504a, 504b has the pathogen-deactivating fibrous material or the multiple-layered structure including the pathogen-deactivating fibrous material described above and shown in FIGS. 1-3 (e.g., 100, 200, 300).

Figure 6:
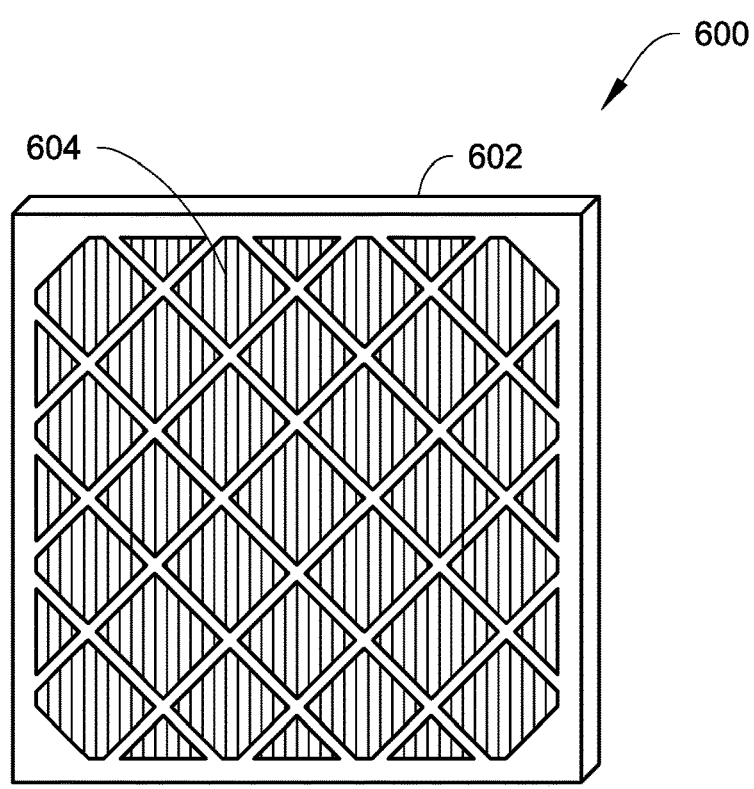
FIG. 6 shows schematic drawings of an air filter device configured to be fitted to an air supply device for deactivating a pathogenic aerosol according to another embodiment.

FIG. 6 shows schematic drawings of an air filter device 600 configured to be fitted to an air supply device for deactivating a pathogenic aerosol according to another embodiment. The air filter device 600 can be configured to fit into, for example, a furnace (forced air system) for supplying air indoors. The air filter device 600 can be configured to fit into, for example, a vehicle cabin filter component. The air filter device 600 includes a frame 602 for retaining one or more layer(s) 604 of filter material(s), wherein one or more of the layer(s) 604 includes a pathogen-deactivating fibrous material or a multiple-layered structure including the pathogen-deactivating fibrous material described above and shown in FIGS. 1-3 (e.g., 100, 200, 300).

Figure 7:
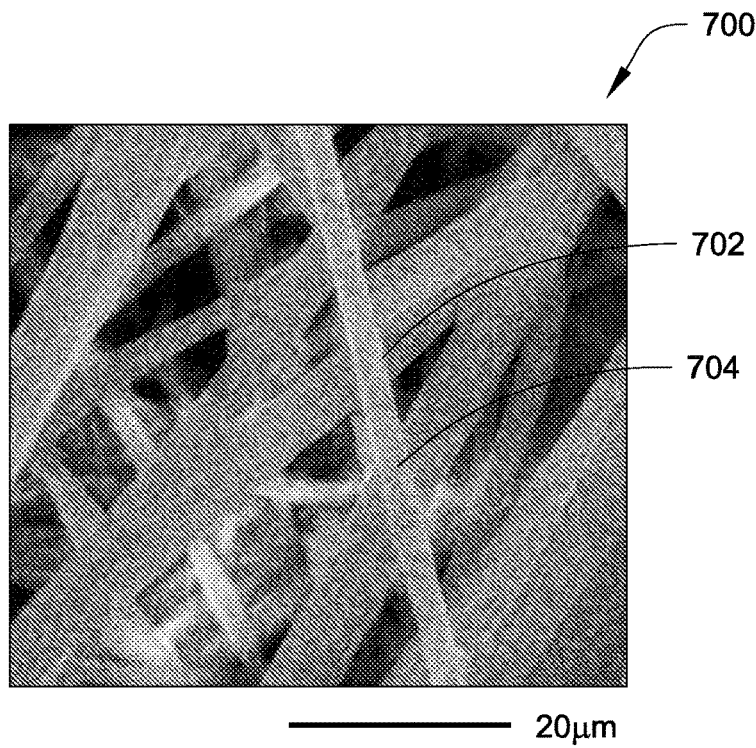
FIG. 7 shows an electron microscope photo image of a fiber material for deactivating a pathogenic aerosol according to an embodiment.

FIG. 7 shows an electron microscope photo image of a fiber material 700 for deactivating a pathogenic aerosol according to an embodiment. The fiber material 700 contains sodium chloride (NaCl) crystals 702 that are coated onto a polypropylene (PP) microfiber 704. The NaCl crystals 702 are obtained from a salt-coating solution containing TWEEN™ 20 (a surfactant) to enhance wetting of saline solution on a surface of the hydrophobic PP microfiber 704. Additional exemplary embodiments are further shown in FIGS. 8-9 and described below.

Figure 8A:
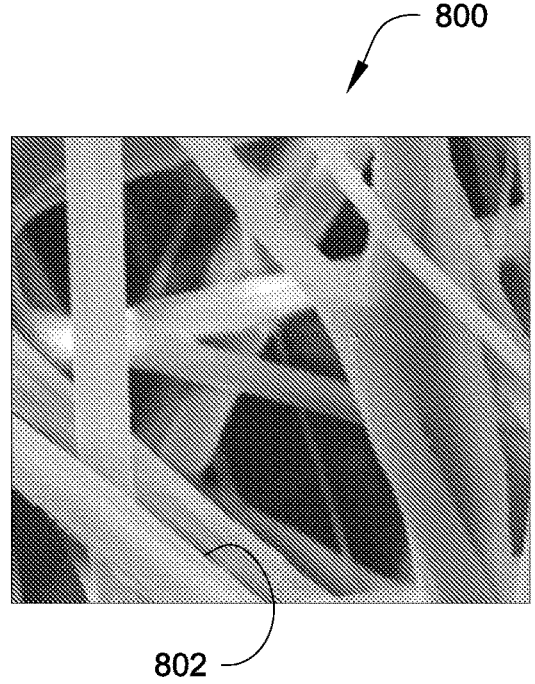
FIG. 8A shows a scanning electron microscopy (SEM) and energy dispersive X-ray (EDX) mapping image of $Filter_{bare}$, which is discussed in greater detail below.
Figure 8B:
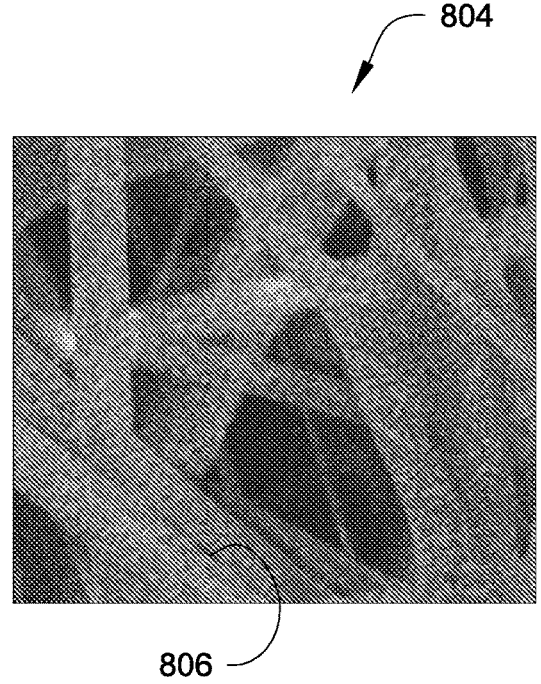
FIG. 8B shows SEM and EDX a mapping image of $Filter_{wet+600\ \mu l}$, which is discussed in greater detail below.
Figure 9A:
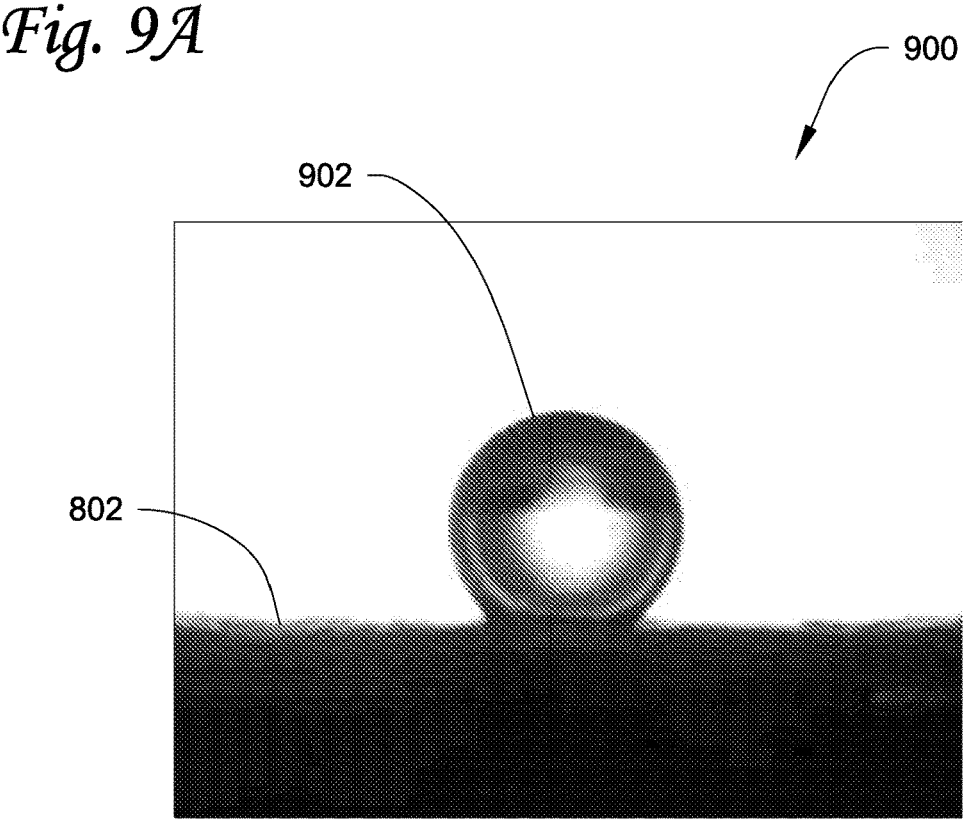
FIG. 9A shows an optical microscope image of an aerosol on the $Filter_{bare}$, which is discussed in greater detail below.
Figure 9B:
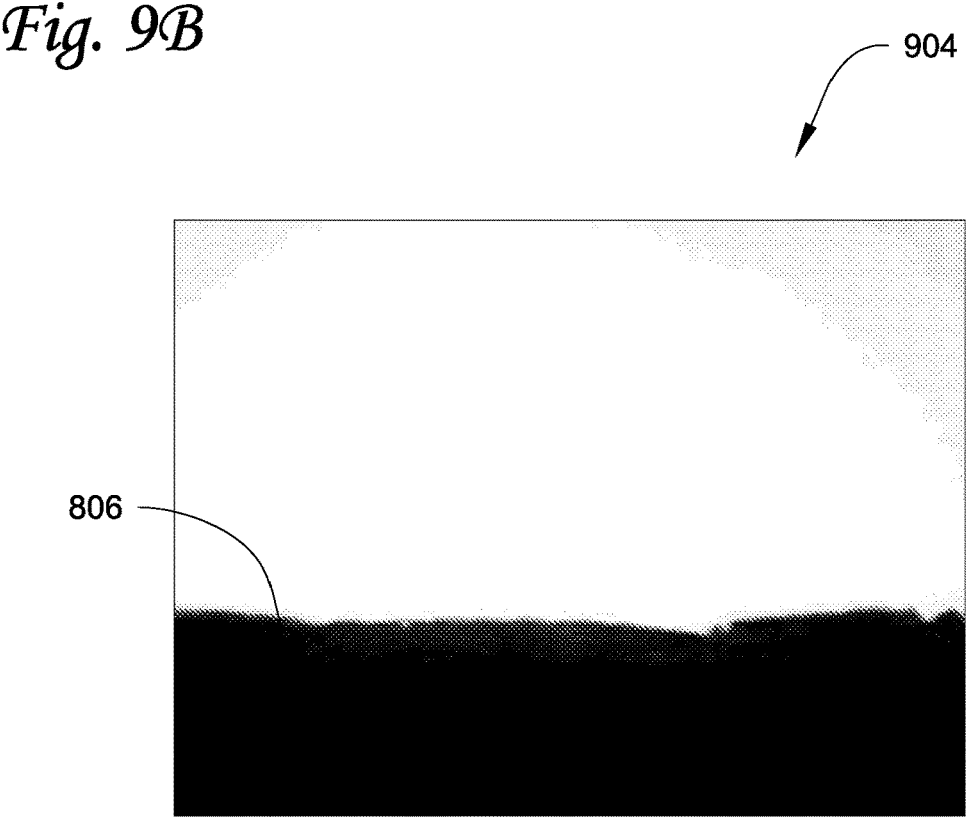
FIG. 9B shows an optical microscope image of an aerosol on the $Filter_{wet+600\ \mu l}$, which is discussed in greater detail below.

FIG. 8A shows SEM and EDX mapping image 800 of a hydrophobic fiber material 802, which lacks any salt crystals on the surface of hydrophobic fibers. In comparison, FIG. 8B shows SEM and EDX a mapping image 804 of the same hydrophobic fiber material as shown in FIG. 8A, except the fiber material 806 shown in FIG. 8B has been coated with a homogeneous NaCl crystal layer. Surface hydrophilicities of the fiber material 802 and the NaCl coated fiber material 806 were investigated by measuring contact angles of aerosols, and the results are shown in FIGS. 9A and 9B, respectively. FIG. 9A shows an optical microscope image 900 of an aerosol 902 on the fiber material 802. The aerosol 902 has a contact angle $\theta_c$ of 133.0±4.7° on the fiber material 802. In contrast, FIG. 9B shows an optical microscope image 904 of an aerosol (not shown) on the NaCl coated fiber material 806. As can be seen in FIG. 9B, there is no aerosol observable on the NaCl material 806. This indicates that the aerosol was adsorbed by the surface of the NaCl coated fiber material 806, and thus the aerosol has a contact angle $\theta_c$ of ~0° on the NaCl coated fiber material 806. These results indicate that the NaCl-crystal coating (in this case, applied with a surfactant) can alter the properties of the surface of the hydrophobic fiber material 802 from being highly hydrophobic ($\theta_c$=133.0±4.7°) to completely hydrophilic ($\theta_c$~0°). Further, the hydrophilic nature of the NaCl crystal coating can significantly improve adhesion of an aerosol to the NaCl coated fiber material 806 relative to an uncoated fiber material 802.

Various embodiments of NaCl coated pathogen-deactivating filters were prepared to compare to an uncoated fiber material (i.e. bare filter or $Filter_{bare}$ herein). The $Filter_{bare}$ in these tests was made of polypropylene microfiber.

The pathogen-deactivating filter was obtained by coating or impregnating a salt-coating solution on the same bare filters as used for $Filter_{bare}$. Thus, the pathogen-deactivating filter is also called salt-crystal coated filter herein. The salt-coating solution was prepared according to the following method. Dissolving NaCl in deionized (DI) water at a temperature of 90° C. under stirring at 400 rpm to obtain a NaCl solution, and then the NaCl solution was then filtered using a filter having 0.22 μm pore size. TWEEN™ 20 (1 v/v %, Fisher Scientific) was then added to the filtered NaCl solution at room temperature under stirring at 400 rpm for 5 min to obtain the salt-coating solution.

The pathogen-deactivating filters, i.e. the salt-crystal coated filters, were obtained in accordance with the following method. Bare filters obtained according to the method as described above were pre-wet in approximately 600 μl of the salt-coating solution by incubation at room temperature for overnight. Then, the bare filters were respectively deposited in 0, 100, 300, 600, 900, and 1200 μl of the salt-coating solution in Petri dishes and then dried in an oven at 37° C. for 1 day. The obtained pathogen-deactivating or salt-coated filters are respectively referred to as $Filter_{wet}$, $Filter_{wet+100\ \mu l}$, $Filter_{wet+300\ \mu l}$, $Filter_{wet+600\ \mu l}$, $Filter_{wet+900\ \mu l}$, and $Filter_{wet+1200\ \mu l}$.

Figure 10:
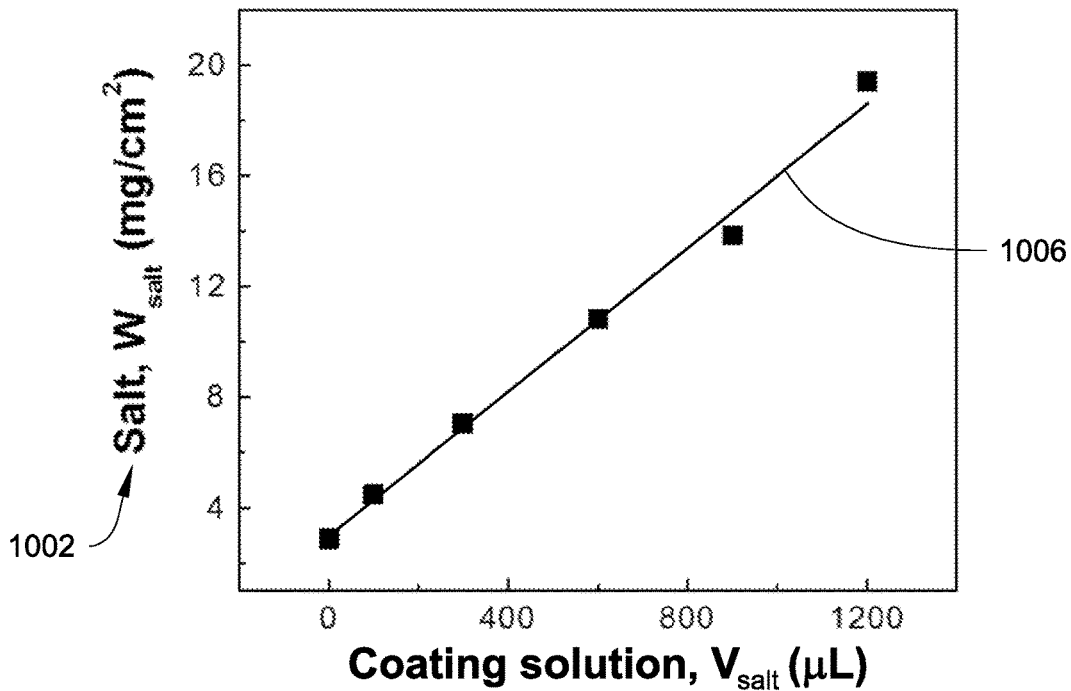
FIG. 10 shows a graph of a relationship between an amount of NaCl crystals per unit area ($mg/cm^2$) coated on a material and a volume ($\mu l$) of a NaCl-coating solution for coating the material, according to an embodiment.

FIG. 10 shows a graph 1000 of a relationship between an amount of NaCl crystals per unit area (mg/cm$^2$) coated on a material and a volume (μl) of a NaCl-coating solution for coating the material, according to an embodiment. The relationship between the amount of NaCl crystals per unit area (mg/cm$^2$, $W_{salt}$) 1002 coated on a supporting member and a volume (μl) of a NaCl-coating solution for coating the supporting member ($V_{salt}$) 1004 is a linear relationship represented by a line 1006. The line 1006 can be regressed to an equation: $W_{salt}=3.011\pm0.013\times V_{sat}$ (n=7)). Thus, the amount of NaCl per unit area on the supporting member can be easily controlled by changing the volume of the NaCl-coating solution used for coating the supporting member, considering that the thickness of the supporting member is constant. The salt-crystal coated supporting member can be further exposed to a spraying process to form another layer of salt crystals.

Figure 11:
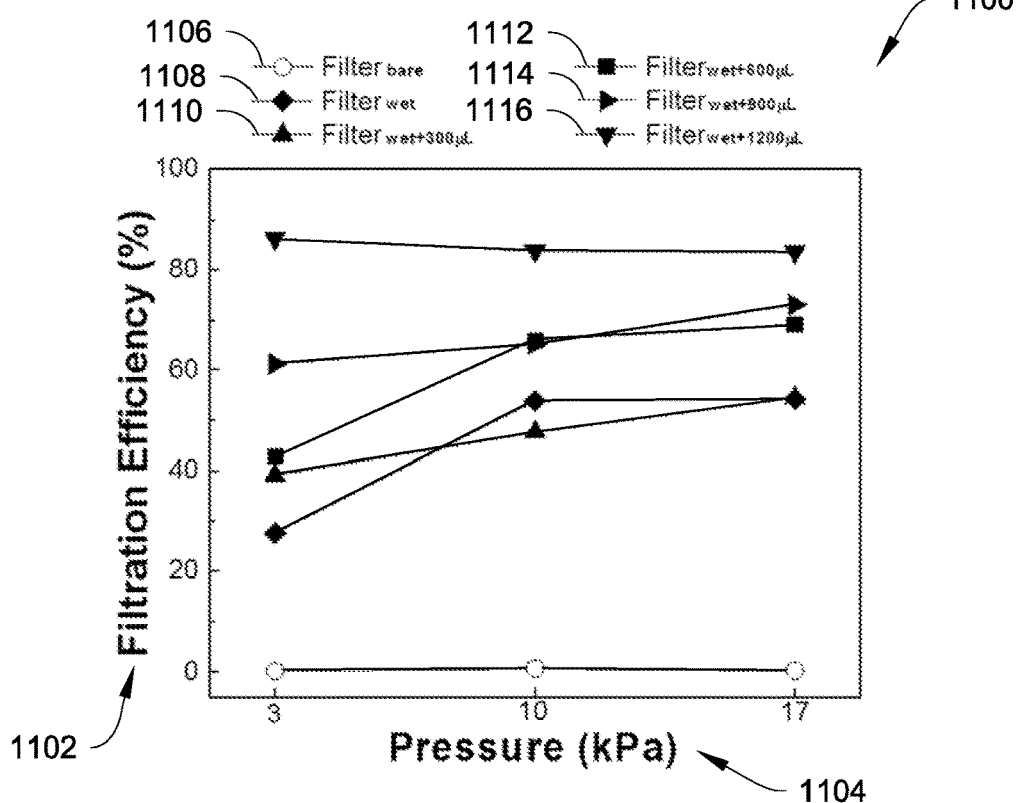
FIG. 11 shows filtration efficiencies data of pathogen-deactivating filters at different pressures, according to some embodiments.

Filtration efficiencies of the embodiments of pathogen-deactivating materials were examined against viral aerosols, and their results are shown in FIG. 11. FIG. 11 illustrates a relationship 1100 that shows filtration efficiencies 1102 of pathogen-deactivating filters at different pressures 1104. Filtration efficiencies of various filters were tested against 2.5-4 μm aerosols containing H1N1 pandemic influenza virus (A/California/04/2009, abbreviated as CA/04) at different environmental pressures. As shown in FIG. 11, the $Filter_{bare}$ (uncoated fiber material) 1106 has nearly 0% filtration efficiency, which indicates that the $Filter_{bare}$ 1106 did not exhibit any significant level of resistance against penetration of virus under pressures from 3 kPa to 17 kPa. In a sharp contrast, the NaCl-crystal coated filters including $Filter_{wet}$ 1108, $Filter_{wet+300\ \mu l}$ 1110, $Filter_{wet+600\ \mu l}$ 1112, $Filter_{wet+900\ \mu l}$ 1114, and $Filter_{wet+1200\ \mu l}$ 1116 showed substantially improved filtration efficiencies under the pressures from 3 kPa to 17 kPa. In particular, the $Filter_{wet+600\ \mu l}$ 1112 exhibited about 43 to 70% filtration efficiency under the pressures from 3 kPa to 17 kPa. The $Filter_{wet+900\ \mu l}$ 1114 exhibited about 60 to 70% filtration efficiency under the pressures from 3 kPa to 17 kPa. The $Filter_{wet+1200\ \mu l}$ 1116 consistently exhibited about 85% filtration efficiency across the pressures from 3 kPa to 17 kPa (one-way ANOVA, P=0.85). The enhanced filtration efficiency of the NaCl-crystal coated filters can be explained by the improved surface hydrophilicity due to the NaCl-crystal coating, resulting in greater adhesion of the aerosols to the NaCl-crystal coated filters than to the bare filter.

To investigate the effects of the filtration efficiency on the protective efficacy of the filters, in vivo experiments were performed using mice intranasally (IN) infected with penetration dosages of the H1N1 virus under breathing pressure (~10 kPa), which results are shown in FIGS. 12-15.

FIG. 12 illustrates a curve chart 1200 that shows body weight changes 1202 of mice after infected with penetration dosages of the virus on pathogen-deactivating filters relative to post infection time 1204. The curve chart 1200 includes curves CA/09 stock, Aerosol, $Filter_{bare}$, $Filter_{wet}$, $Filter_{wet+600\ \mu l}$, and $Filter_{wet+1200\ \mu l}$. The curves $Filter_{bare}$, $Filter_{wet}$, $Filter_{wet+600\ \mu l}$, $Filter_{wet+1200\ \mu l}$ respectively show the body weight changes of mice infected with aerosolized CA/09 virus recovered from the $Filter_{bare}$, the $Filter_{wet}$, the $Filter_{wet+600\ \mu l}$, and the $Filter_{wet+1200\ \mu l}$. The curves CA/09 stock and Aerosol show body weight changes of mice directed infected with a lethal dosage of CA/09 virus and aerosolized CA/09 virus, respectively. As can be seen, $Filter_{wet}$, $Filter_{wet+600\ \mu l}$, and $Filter_{wet+1200\ \mu l}$ regained body weight 10 days following infection. In contrast, $Filter_{bare}$ exhibited rapid body weight loss, which is comparable to that exhibited by CA/09 stock and Aerosol. This is in agreement with the observed 0% filtration efficiency for the $Filter_{bare}$ shown in FIG. 11.

Referring to FIG. 13, a curve chart 1300 shows survival rates 1302 of the mice after infected with penetration dosages of the virus on pathogen-deactivating filters relative to post infection time 1304. The curve chart 1400 includes curves CA/09 stock, Aerosol, $Filter_{bare}$, $Filter_{wet}$, $Filter_{wet+600\ \mu l}$, and $Filter_{wet+1200\ \mu l}$. As can be seen, the curves $Filter_{wet}$, $Filter_{wet+600\ \mu l}$, and $Filter_{wet+1200\ \mu l}$ exhibit 100% survival rate, which indicates the mice infected with virus recovered from the $Filter_{wet}$, the $Filter_{wet+600\ \mu l}$, and the $Filter_{wet+1200\ \mu l}$ has 100% survival rate. In contrast, the curves CA/09 stock, Aerosol, and $Filter_{bare}$ display 0% survival rate after about 11 post infection days, which indicate the mice infected with CA/09 virus, aerosolized CA/09 virus, and virus recovered from the $Filter_{bare}$ were all dead within about 11 days following infection.

Figures 14, 15:
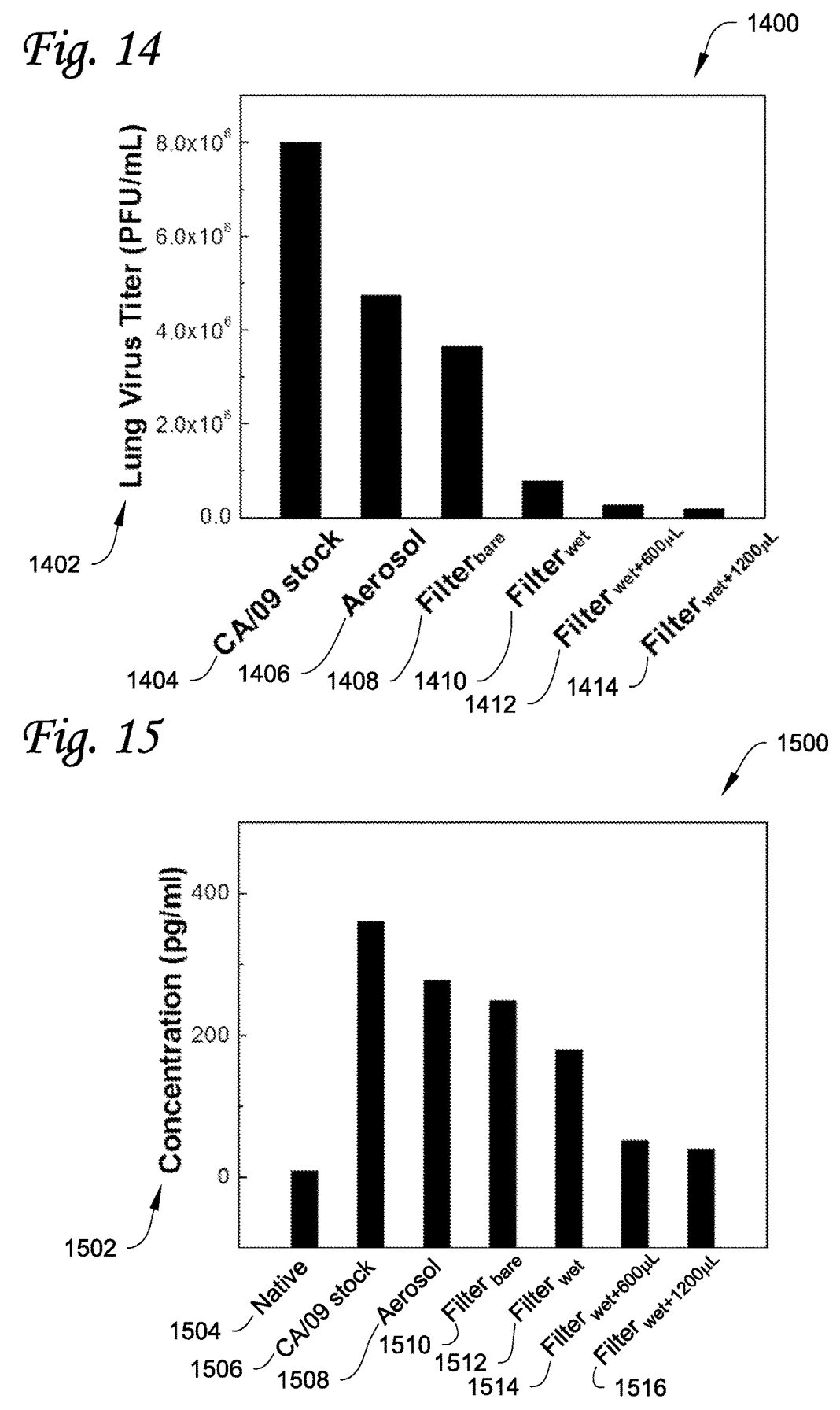

FIG. 14 illustrates a column chart 1400 that shows lung virus titers 1402 of the mice at day 4 following infection with penetration dosages of the virus on pathogen-deactivating filters. The column chart 1500 include columns CA/09 stock 1404, Aerosol 1406, $Filter_{bare}$ 1408, $Filter_{wet}$ 1410, $Filter_{wet+600\ \mu l}$ 1412, and $Filter_{wet+1200\ \mu l}$ 1414. As can be seen, the columns $Filter_{wet}$ 1410, $Filter_{wet+600\ \mu l}$ 1412, and $Filter_{wet+1200\ \mu l}$ 1414 display significantly lower lung virus titers than the columns CA/09 stock 1404, Aerosol 1406, and $Filter_{bare}$ 1408 (t-test, P<0.005). These results indicate that the lung virus titers from the mice infected with aerosolized CA/09 virus recovered from the $Filter_{bare}$, the $Filter_{wet+600\ \mu l}$, and the $Filter_{wet+1200\ \mu l}$ have significantly lower levels of lung viral titers than those from the mice infected with CA/09 virus, aerosolized CA/09 virus, and aerosolized CA/09 virus recovered the $Filter_{bare}$. It is also observed that the mice represented by the columns CA/09 stock 1404, Aerosol 1406, and $Filter_{bare}$ 1408 exhibited severe lung infection 4 days following infection.

FIG. 15 illustrates a column chart 1500 that shows lung inflammatory cytokine interferon-γ (IFN-γ) level 1502 in mice after infected penetration dosage of the virus on pathogen-deactivating filters. The column chart 1500 include native 1504, CA/09 stock 1506, Aerosol 1508, Filter$_{bare}$ 1510, Filter$_{wet}$ 1512, Filter$_{wet+600\ \mu l}$ 1514, and Filter$_{wet+1200\ \mu l}$ 1516. The column native group 1504 shows IFN-γ level in the native mice that were not infected with the virus, serving as the blank control. The columns CA/09 stock 1506, Aerosol 1508, and Filter$_{bare}$ 1510 respectively show IFN-γ levels in the mice infected with CA/09 virus, aerosolized CA/09 virus, and aerosolized CA/09 virus recovered from the Filter$_{bare}$. The columns Filter$_{wet}$ 1512, Filter$_{wet+600\ \mu l}$ 1514, and Filter$_{wet+1200\ \mu l}$ 1516 respectively show IFN-γ levels in the mice infected with aerosolized CA/09 virus recovered from the Filter$_{wet}$, the Filter$_{wet+600\ \mu l}$, and the Filter$_{wet+1200\ \mu l}$. As can be seen, the columns Filter$_{wet}$ 1512, Filter$_{wet+600\ \mu l}$ 1514, and Filter$_{wet+1200\ \mu l}$ 1516 display IFN-γ levels comparable to that of the column native 1504, which indicates that the mice infected with viruses recovered from the salt-crystal coated filters have almost the same IFN-γ level as the native mice that were not infected with the virus. As also can be seen, the columns CA/09 stock 1506, Aerosol 1508, Filter$_{bare}$ 1510 display significantly higher level of IFN-γ than the columns Filter$_{wet}$ 1512, Filter$_{wet+600\ \mu l}$ 1514, Filter$_{wet+1200\ \mu l}$ 1516, and native group 1504. These results demonstrate that the salt-crystal coated filters can effectively provide sufficient protection against lethal viral aerosols.

Further, the effects of the salt-crystal coating on the virus in aerosols adsorbed on the filters were investigated by in vitro virus stability test. The in vitro virus stability was characterized by measuring hemagglutinin activity (HA) and virus titers at the same concentration as the lethal dose. The conformational stability of antigenic proteins was characterized by measuring intrinsic fluorescence using 0.1 mg/ml of virus suspension. The same concentration of recovered viruses from the filters was used, and, in the case of bare filters, viral aerosols exposure was conducted in the absence of pressure due to 100% penetration of viral aerosols.

Figure 16:
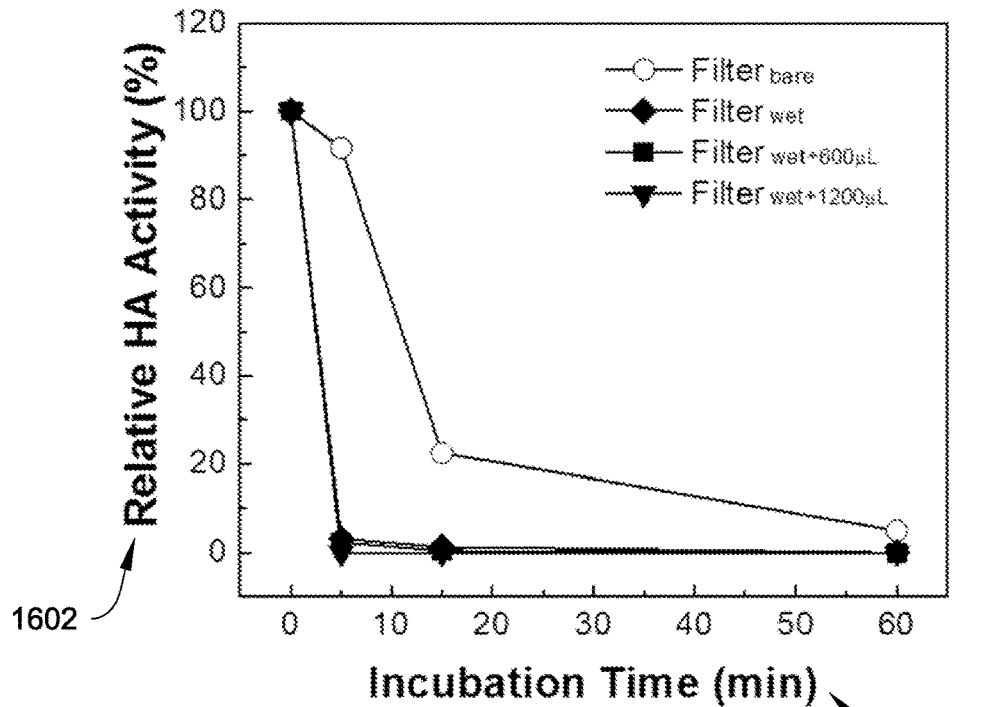
FIG. 16 shows relative HA activity of the virus in viral aerosols on pathogen-deactivating filters over incubation time, according to some embodiments.

Referring to FIG. 16, a curve chart 1600 shows relative HA activity 1602 of virus in viral aerosols on pathogen-deactivating filters over incubation time 1604. The curve chart 1600 includes curves Filter$_{bare}$, Filter$_{wet}$, Filter$_{wet+600\ \mu l}$, and Filter$_{wet+1200\ \mu l}$, which respectively show the relative HA activities of the virus on the Filter$_{bare}$, the Filter$_{wet}$, the Filter$_{wet+600\ \mu l}$, and the Filter$_{wet+1200\ \mu l}$. As can be seen, the columns Filter$_{wet}$, Filter$_{wet+600\ \mu l}$, and Filter$_{wet+1200\ \mu l}$ display almost 0% of HA activities 5 minutes following absorption onto the NaCl-crystal coated filters. These results indicate that the virus on the salt-crystal coated filters completely loses its HA activity five (5) minutes after being absorbed thereon. This is in a sharp contrast with only 8% HA activity loss for the virus on the Filter$_{bare}$, as shown in the curve Filter$_{bare}$. These data indicate that the virus becomes highly unstable on the NaCl-crystal coated filters. Based on the above results, it can be reasoned that the rapid loss of HA activity and viral infectivity on the salt-crystal coated filters can be attributed to the NaCl-crystal coating. That is, the NaCl-coated filters can significantly deactivate the virus absorbed thereon.

Figure 17:
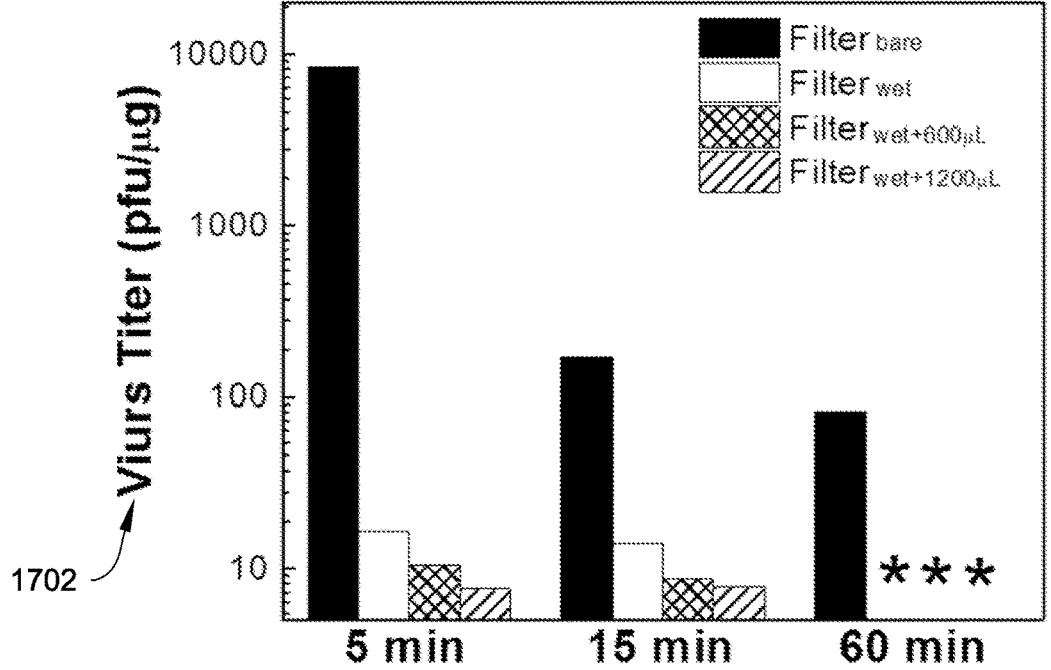
FIG. 17 shows virus titer data of viral aerosols incubated on pathogen-deactivating filters for 5 minutes, 15 minutes, and 60 minutes, according to some embodiments.

The effect of the NaCl-crystal coated filters on virus stability is further evidenced by measuring virus titer relative to the incubation time of the virus on the filters. Viral aerosols are absorbed or incubated on the filters for 5 minutes, 15 minutes, and 60 minutes. Afterward, the titers of the viruses in the viral aerosols were measured. The results are shown in FIG. 17. A column chart 1700 shows virus titer 1702 of viral aerosols absorbed or incubated on the Filter$_{bare}$, the Filter$_{wet}$, the Filter$_{wet+600\ \mu l}$, and the Filter$_{wet+1200\ \mu l}$ for some time 1704 (5 minutes, 15 minutes, and 60 minutes).

As can be seen, at the incubation time of 5, the Filter$_{wet}$, the Filter$_{wet+600\ \mu l}$, and Filter$_{wet+1200\ \mu l}$ display negligible levels of viral titers compared to the Filter$_{bare}$ (t-test, P<0.001).

At the incubation time of 15 minutes, the Filter$_{wet}$, the Filter$_{wet+600\ \mu l}$, and Filter$_{wet+1200\ \mu l}$ display negligible levels of viral titers compared to the Filter$_{bare}$ (t-test, P<0.001).

At the incubation time of 60 minutes, the Filter$_{wet}$, Filter$_{wet+600\ \mu l}$, and Filter$_{wet+1200\ \mu l}$ appear to display undetectable virus titers indicated by the symbol "*" in the column chart 1700. These results indicate that the aerosolized viruses on the NaCl-crystal coated filters are all deactivated at the incubation time of 60 minutes. In contrast, the aerosolized virus on the Filter$_{bare}$ still exhibits a virus titer of more than 100 pfu/μg at the incubation time of 60 minutes.

These data demonstrate that the virus was severely damaged on the NaCl-crystal coated filters even at 5 minutes of incubation. According to microscopic analysis, drying time for the aerosols was about 3 min, and thereby it can be reasoned that the physical damage of the virus at 5 minutes is due to drying-induced salt crystallization.

Figure 18:
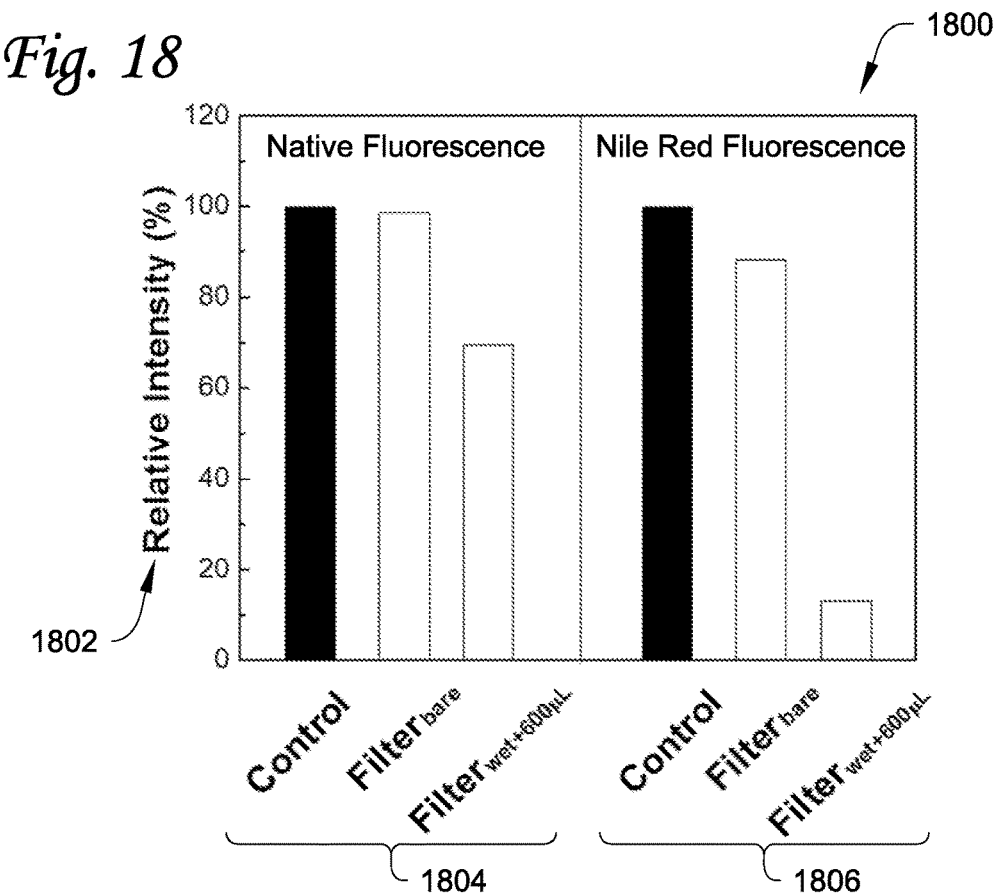
FIG. 18 shows a data chart of relative intensities of native fluorescence and Nile red fluorescence for the virus recovered from pathogen-deactivating filters after 60 minutes of incubation, according to some embodiments.

FIG. 18 illustrates a column chart 1800 that shows relative intensity 1802 of native fluorescence 1804 and Nile red fluorescence 1806 for the virus recovered from pathogen-deactivating filters. The column chart 1800 includes control, Filter$_{bare}$ and Filter$_{wet+600\ \mu l}$ for native fluorescence test group 1804; and control, Filter$_{bare}$ and Filter$_{wet+600\ \mu l}$ for Nile red fluorescence test group 1806. As can be seen, for the native fluorescence test group 1804, the Filter$_{wet+600\ \mu l}$ displays significantly lower levels of native fluorescence than the columns Filter$_{bare}$ and control. For the Nile red fluorescence test group 1806, the Filter$_{wet+600\ \mu l}$ displays significantly lower levels of Nile red fluorescence than the Filter$_{bare}$ and control. These results indicate that the virus recovered from the Filter$_{wet+600\ \mu l}$ display significantly lower levels of native fluorescence and Nile red fluorescence than the virus recovered from Filter$_{bare}$ and the native virus. These results also suggest that the Filter$_{wet+600\ \mu l}$ can cause a profound conformational change to viral antigenic proteins and destabilize viral envelope.

Effects of the osmotic pressure on the virus stability during drying of the pathogenic aerosols were also investigated. The viruses collected in the aerosols on the Filter$_{wet+600\ \mu L}$ displays visible morphological transformation compared to the virus in the aerosols on the Filter$_{bare}$. This can be attributed to the high salt/surfactant concentration and the concurrent osmotic pressure, which destabilizes viruses. The marked virus destabilization effect of the salt-crystal coated fibers can be attributed to the combined effects of increasing osmotic pressure, electrostatic interaction, and evaporation-induced salt re-crystallization. To verify the above virus destabilization effect of the salt-crystal coated filters, in vivo study was performed by infecting mice with the virus incubated for 60 minutes on the filters including Filter$_{bare}$, Filter$_{wet}$, Filter$_{wet+600\ \mu l}$, and Filter$_{wet+1200\ \mu l}$, which results are shown in FIGS. 19 and 20.

Figure 19:
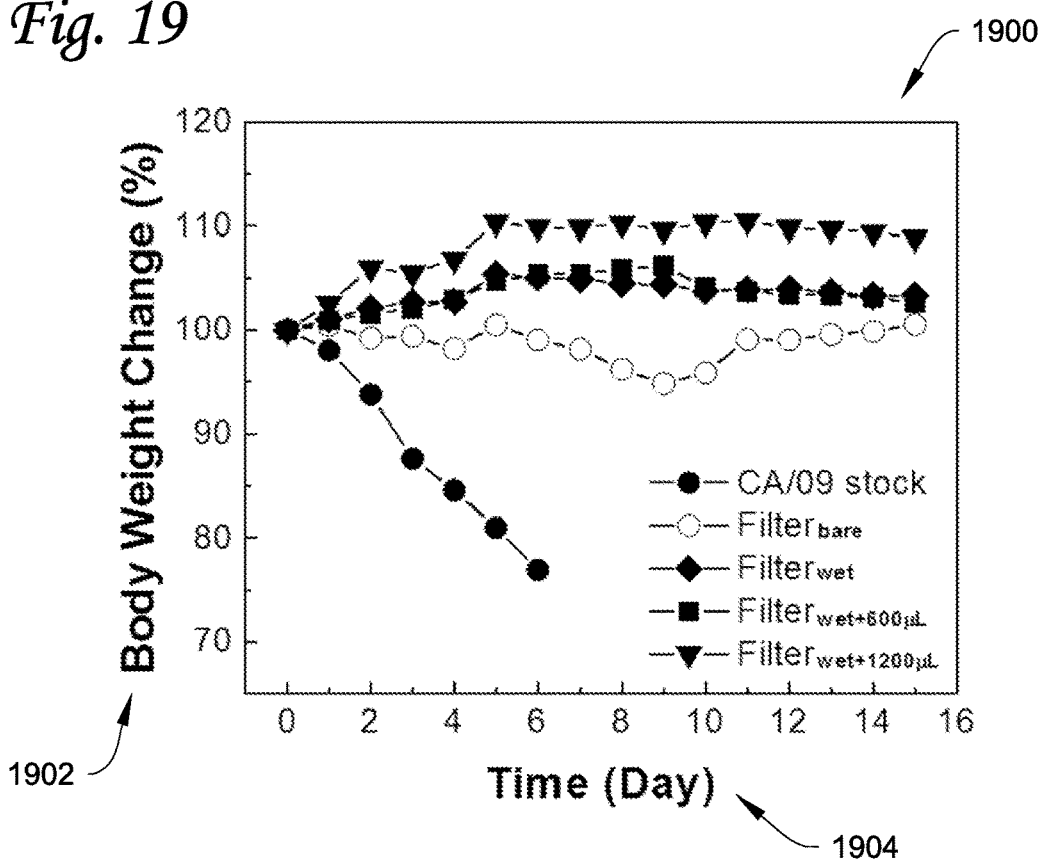
FIG. 19 shows body weight change data of mice infected with the virus incubated for 60 minutes on pathogen-deactivating filters relative to post infection time, according to some embodiments.

FIG. 19 shows a curve chart 1900 that shows body weight change 1902 of mice infected with the virus incubated for 60 minutes on pathogen-deactivating filters relative to post infection time 1904. The curve chart 1900 includes curves CA/09 stock, Filter$_{bare}$, Filter$_{wet}$, Filter$_{wet+600\ \mu l}$, and Filter$_{wet+1200\ \mu l}$. The curve CA/09 stock shows the body weight changes of mice directly infected with the aerosolized CA/09 virus. The curves Filter$_{bare}$, Filter$_{wet}$, Filter$_{wet+600\ \mu l}$, and Filter$_{wet+1200\ \mu l}$ respective show the body weight changes of mice infected with the virus recovered from the Filter$_{bare}$, the Filter$_{wet}$, the Filter$_{wet+600\ \mu l}$, and the Filter$_{wet+1200\ \mu l}$. As can be seen, the curves Filter$_{wet}$, Filter$_{wet+600\ \mu l}$, and Filter$_{wet+1200\ \mu l}$ display an increasing weight after infection and gains about 5 to 10% of body weight at day 9 following infection. In contrast, the curve CA/09 stock reveals a rapid decrease of body weight loss after infection, and mice are even dead 6 days following infection.

Figures 20, 21:
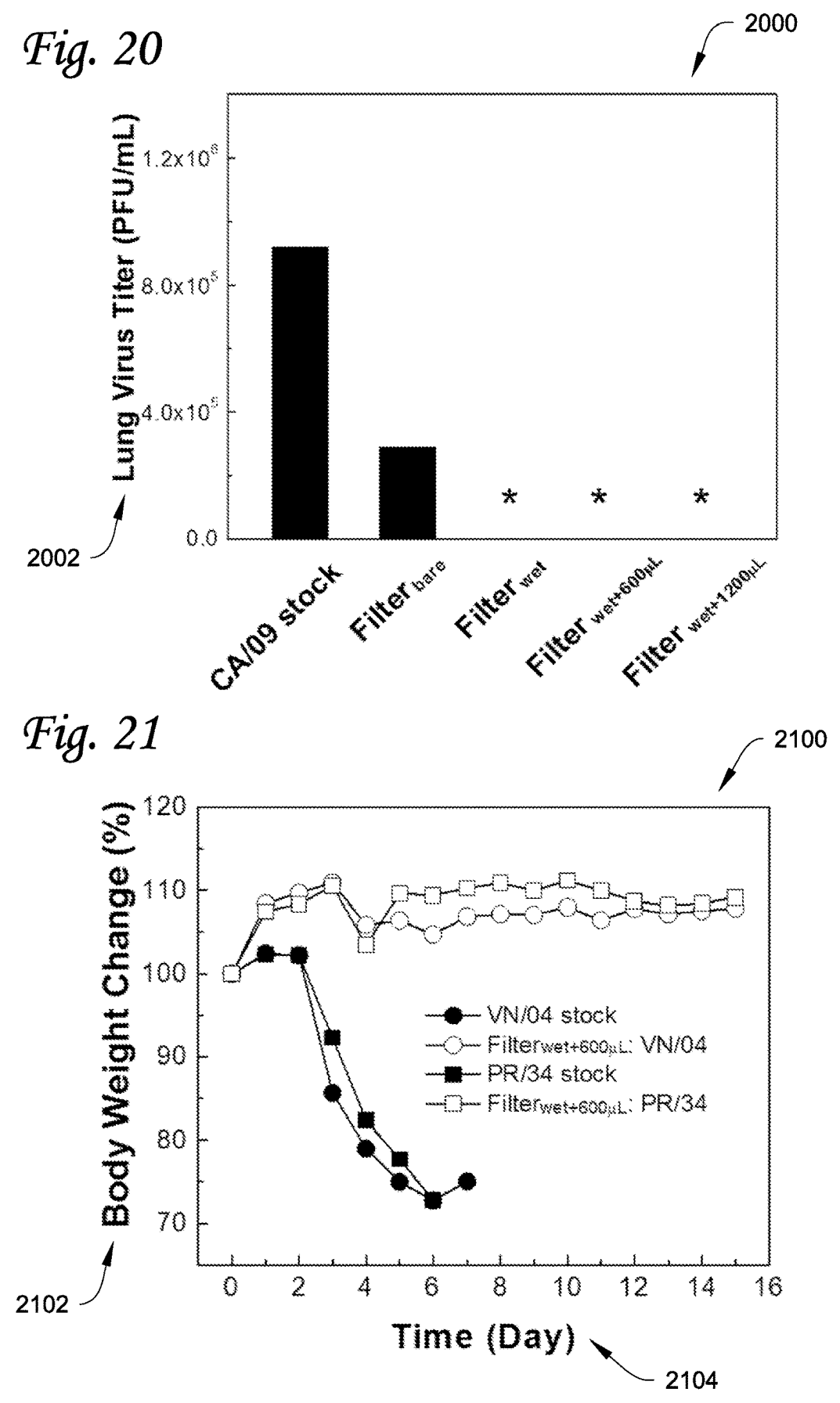

FIG. 20 illustrates a column chart 2000 that shows lung virus titer 2002 of mice infected with CA/09 virus before and after incubated on the salt-crystal coated filters for 60 minutes. The column chart 2000 includes columns for CA/09 stock, Filter$_{bare}$, Filter$_{wet}$, Filter$_{wet+600\ \mu l}$, and Filter$_{wet+1200\ \mu l}$. The column for CA/09 stock shows the lung virus titer of mice infected with the aerosolized CA/09 virus before being incubated on the salt-crystal coated filters, which serves a control. The columns Filter$_{bare}$, Filter$_{wet}$, Filter$_{wet+600\ \mu l}$, and Filter$_{wet+1200\ \mu l}$ respectively show lung virus titers of mice infected with CA/09 virus recovered from the Filter$_{bare}$, the Filter$_{wet}$, the Filter$_{wet+600\ \mu l}$, and the Filter$_{wet+1200\ \mu l}$. As can be seen, the columns for Filter$_{wet}$, Filter$_{wet+600\ \mu l}$, and Filter$_{wet+1200\ \mu l}$ do not exhibit detectable lung virus titer. In contrast, the column for Filter$_{bare}$ displays lung virus titer of about $4.0 \times 10^5$ PFU/ml. In further contrast, the column for CA/09 stock shows that the lung virus titer of more than $8.0 \times 10^5$ PFU/ml. These data evidence that the salt-crystal coated filters possess significant advantages over the bare filter in personal protection, as the salt-crystal coated filters can destroy the virus adsorbed thereon via the salt re-crystallization process.

Broad-spectrum protection of the salt-crystal coated filters against multiple subtypes of viral aerosols was evaluated by investigating both in vivo lethal infectivity of the penetrated virus and infectivity of the virus collected on the filters during in vitro filtration. The results are shown in FIGS. 21 and 22.

FIG. 21 illustrates a curve chart 2100 that shows body weight change 2102 of mice infected with penetration dosage of viruses on a pathogen-deactivating filter relative post infection time 2104. The curve chart 2100 includes data curves for VN/04 stock, PR/34 stock, Filter$_{wet+600\ \mu l}$: VN/04 2210, and Filter$_{wet+600\ \mu l}$: PR/34. The data curves for VN/04 stock and PR/34 stock respectively show the body weight changes of mice infected with the lethal dose of aerosolized VN/04 and PR/34 viruses. The data curve for Filter$_{wet+600\ \mu l}$: VN/04 shows the body weight change of the mice infected with penetration dosage of VN/04 virus through the Filter$_{wet+600\ \mu l}$. The data curve for Filter$_{wet+600\ \mu l}$: PR/34 shows the body weight changes of the mice infected with penetration dosage of PR/34 virus through the Filter$_{wet+600\ \mu l}$. As can be seen, the data curves for Filter$_{wet+600\ \mu l}$: VN/04 and Filter$_{wet+600\ \mu l}$: PR/34 show that there was no weight loss. In contrast, the data curves for VN/04 stock and PR/34 stock 2208 show rapid weight loss following infection.

Figures 22, 23:
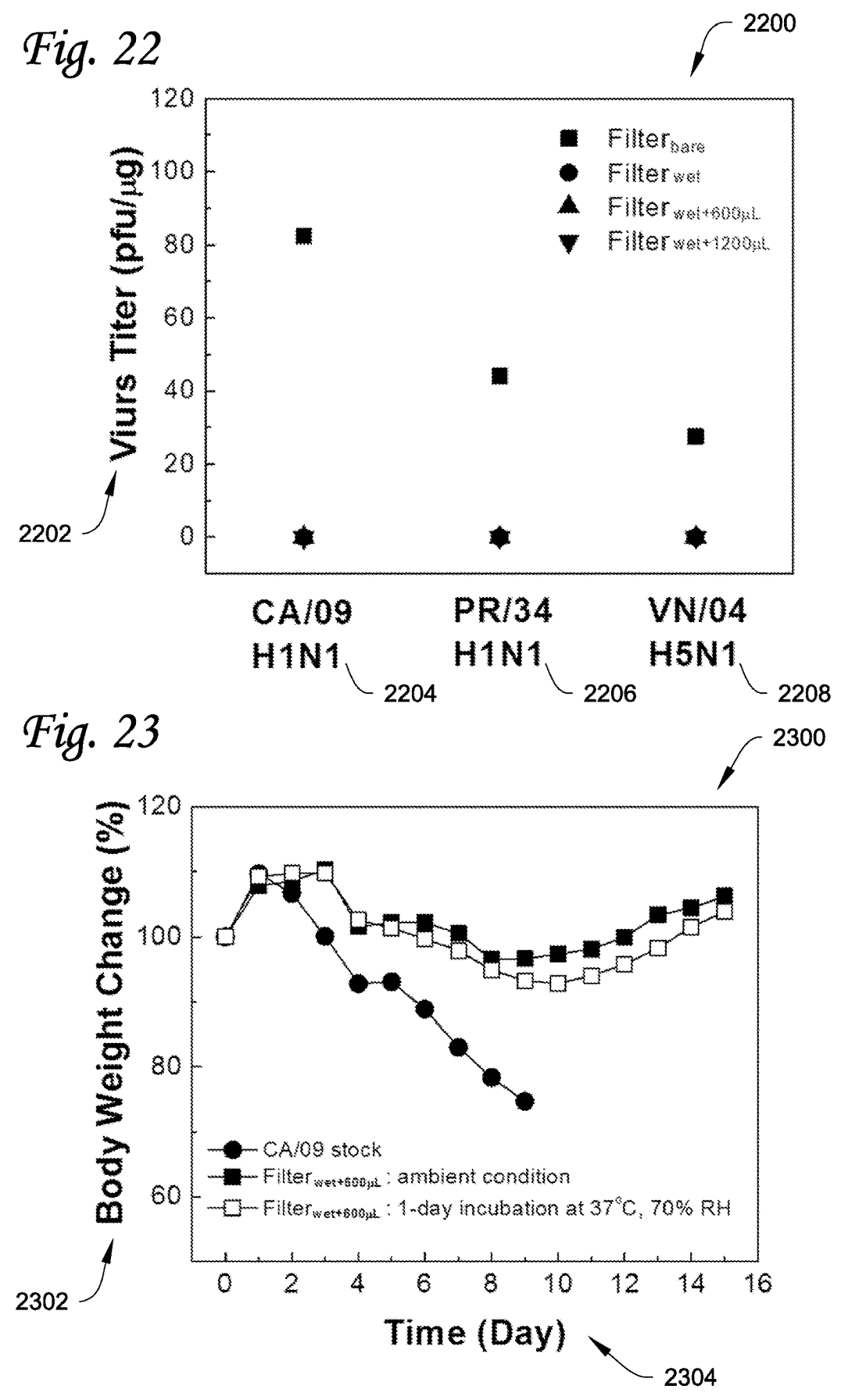

FIG. 22 illustrates a chart 2200 that shows virus titers 2202 for aerosolized CA/09 H1N1 2204, PR/34 H1N1 2206 and VN/04 H5N1 2208 incubated on the Filter$_{bare}$, the Filter$_{wet}$, the Filter$_{wet+600\ \mu l}$, and the Filter$_{wet+1200\ \mu l}$. As can be seen, aerosolized CA/09 H1N1 2204 on Filter$_{bare}$ exhibits 80 pfu/g of virus titer, but aerosolized CA/09 H1N1 2204 on Filter$_{wet}$, Filter$_{wet+600\ \mu l}$, and Filter$_{wet+1200\ \mu l}$ exhibit almost 0 virus titer. Similarly, aerosolized PR/34 H1N1 2206 on Filter$_{bare}$ exhibits 45 pfu/g of virus titer, but aerosolized PR/34 H1N1 2206 on Filter$_{wet}$, Filter$_{wet+600\ \mu l}$, and Filter$_{wet+1200\ \mu l}$ have almost 0 virus titer. Likewise, aerosolized VN/04 H5N1 2208 on Filter$_{bare}$ exhibits 25 pfu/μg of virus titer, but aerosolized VN/04 H5N1 2208 on Filter$_{wet}$, Filter$_{wet+600\ \mu l}$, and Filter$_{wet+1200\ \mu l}$ have almost 0 virus titer. These data evidence that the salt-crystal coated filters can deactivate viruses irrespective of the viral subtypes, indicating that the salt-crystal coated filters can deactivate viruses in a non-specific way.

The stability of the salt-crystal coating was tested under harsh environmental conditions, which results are shown in FIGS. 23 and 24. FIG. 23 illustrates a curve chart 2300 that shows body weight change 2302 of mice relative to post infection time 2304. The curve chart 2300 include data curves for CA/09 stock, Filter$_{wet+600\ \mu l}$, and Filter$_{wet+600\ \mu l'}$. The data curve for CA/09 stock shows body weight changes of mice infected with the aerosolized CA/09 virus, which serves as the control. The data curve for Filter$_{wet+600\ \mu l}$ shows body weight change of mice infected with penetration dosage of the aerosolized CA/09 virus that is incubated on a Filter$_{wet+600\ \mu l}$ stored at ambient condition. The data curve for Filter$_{wet+600\ \mu l'}$ shows body weight change of mice infected with penetration dosage of aerosolized CA/09 virus that is incubated on a Filter$_{wet+600\ \mu l}$ that had been stored at 37° C. and 70% relative humidity (RH) for 1 day. As can be seen, the data curve for Filter$_{wet+600\ \mu l'}$ shows comparable body weight changes to the data curve for Filter$_{wet+600\ \mu l}$, indicating that the Filter$_{wet+600\ \mu l}$ is at least stable at 37° C. and 70% relative humidity (RH) for 1 day. Even after 15 days of incubation, it was found that salt crystals remain on the Filter$_{wet+600\ \mu l}$, despite the change in grain orientation due to recrystallization. Therefore, the stability of the salt-crystal coating is not compromised by high temperature and humidity, eliminating any concern over the stability of long-term storage and use in such environmental conditions.

FIG. 24 illustrates a curve chart 2400 that shows survival rate 2402 of mice infected with penetration dosages of CA/09 virus on a pathogen-deactivating filter before and after exposure to 37° C. and 70% RH for 1 day relative to the post infection time 2404. The curve chart 2400 includes data curves for CA/09 stock, Filter$_{wet+600\ \mu l}$, and Filter$_{wet+600\ \mu l'}$. The data curve for CA/09 stock shows the survival rate of mice directly infected with a lethal dose of aerosolized CA/09 virus, which serves as the control. The data curve for Filter$_{wet+600\ \mu l}$ shows the survival rate of mice infected with a penetration dosage of CA/09 virus on the Filter$_{wet+600\ \mu l}$ that is stored at ambient condition. The data curve for Filter$_{wet+600\ \mu l'}$ shows the survival rate of mice infected with a penetration dosage of CA/09 virus on the Filter$_{wet+600\ \mu l}$ that has been incubation at 37° C. and 70% relative humidity (RH) for 1 day. As can be seen, the data curve for Filter$_{wet+600\ \mu l'}$ exhibits the same 100% survival rate as the data curve for Filter$_{wet+600\ \mu l}$ at 8 days following infection. In contrast, the data curve for CA/09 stock displays lower than 20% survival rate at 8 days following infection. These results demonstrate that salt crystal coating can assure protection even under harsh environmental conditions, which allows development of long-term stable, versatile airborne pathogen negation system.

FIG. 25 shows a flowchart of an embodiment of a method 2500 for manufacturing a pathogen-deactivating filter material. The method 2500 is for coating or impregnating a supporting member (e.g., a mesh, a fiber, a fabric (woven or nonwoven), a coating, a porous membrane, a filter material, an existing layer in an air filter, etc.) with salt crystals or one or more salt crystal coating layer(s). In an embodiment, the method 2500 is used to coat the entire outer surface of fibrous materials with one or more types of salt crystals.

In step 2502, a supporting member is coated with a salt-coating solution to obtain a coated supporting member. The supporting member can be hydrophobic or hydrophilic. In an embodiment, the supporting member is a nonwoven spunbond or meltblown polypropylene (PP) fabric. In an embodiment, the supporting member is a porous membrane.

The salt-coating solution includes organic or inorganic salt (and/or their ions). In an embodiment, the salt-coating solution can also include an additive. In an embodiment, the salt-coating solution can further include a surfactant. If the coating surface of the supporting member is hydrophilic, an embodiment of the method uses a salt-coating solution which contains no surfactant. In another embodiment, the method uses a salt-coating solution which contains very small amount of surfactant. If the coating surface of the supporting member is hydrophobic, an embodiment of the method uses a salt-coating solution which contains a surfactant. The salt concentration in the salt-coating solution can be those described herein, but not necessarily limited to only those described herein. The concentration of the salt can be adjusted to make continuous salt crystal coating or discontinuous nano/micro salt crystal disposed on the outer surface of the supporting member, and to control a thickness or crystal size of the resultant salt crystal coating.

In step 2504, the salt coated supporting member is dried to obtain a dried filter that is coated or impregnated with salt crystals. The drying can take place at room temperature or an elevated temperature that is below the melting temperature of the supporting member. At the end of the drying process, the pathogen-deactivating filter material is produced.

In optional step 2506, the pathogen-deactivating filter material is installed in a multi-layered structure or an air filter device (e.g., a mask, a respirator, a car cabin air purifier, a forced air filter for a building, etc.) FIG. 26 shows a specific embodiment of a manufacturing process 2600 for the pathogen-deactivating salt-coated filter material. The process 2600 is described in several parts or steps, labeled A, B, C, D, E, F, G, and H in FIG. 26. Not all of these several parts are absolutely required to finish the manufacturing process 2600, and these parts can be repeated. In general, the process 2600 starts at step A; then optionally can perform step B; either step C or D is next (and if step C is taken, then step D can be taken after step C); then any one of steps E, F, or G can be taken next; and then proceed to step H which results in the finished pathogen-deactivating filter material with a salt coating. Each of the steps A, B, C, D, E, F, G, and H are described in detail below.

Step A: Start with a bare filter material or supporting member (i.e. not salt coated).

Step B: Plasma treatment process (glow discharge treatment) can be performed on the bare filter material, as an option. This process increases surface hydrophilicity. Low-pressure plasma can be used to modify the surface of filters. The plasma can include but without limited to air, $N_2$, Ar, $O_2$, etc. In some embodiments, the plasma treatment allows eliminating or reducing the use of surfactant.

Step C: Remove air bubbles from the filter material or supporting member. In an embodiment, this can be accomplished with a pre-wetting step, where air bubbles are removed from the supporting member by soaking in a salt-coating solution overnight. In another embodiment, the air pockets (bubbles) can be removed mechanically by gently smoothing surfaces of the supporting member out using a device having a flat surface or blade.

Step D: As an optional step, salt formulations can be directly applied to the supporting member's surface (or filter material surface) by spraying a salt formulation or applying droplets of the salt formulation. Droplet size of the coating solution can be 100 nm to 1 mm.

Steps E, F, G: Pre-wet or spray-coated filters can be dried at ambient conditions or at elevated temperatures (below melting temperature of filter materials) in a closed-bottom container (E), in a mesh-bottom container (F), or in a holder with open top and bottom (G) to form salt-crystal coating on filters. Different containers, drying methods, and conditions can be used to control the salt crystallization behavior and to have a uniform salt coating on filters. In the case of drying in a closed-bottom container, pre-wet filters can be dried in the presence of a salt coating formulation with different volumes. The advantage of this approach is that if needed, an extra saline solution can be added into the container during drying of the filter, which in turn increases the amount of salt coated onto the supporting member.

During the drying step, the filter container can be on a rocking or shaking or a rotating platform to induce uniform salt crystal formation on the supporting member. In an embodiment, the container can also be stationary without being subject to motion, and thereby the pre-wet or spray-coated supporting member will dry on a flat bottom of the container.

In step G, the filter can be placed in a holder (described below and shown in FIGS. 27 and 28) can be loaded into a filter holder rack and rotated during drying.

In an embodiment, a pre-wet or a spray-coated supporting member can be dried at an ambient condition or at an elevated temperature that is below the melting temperature of the supporting member to obtain the dried filter.

Step H: A salt-coated filter material is achieved. However, the product can be further exposed to step D (spraying process) to form another layer of salt crystals (with the same salt or different salt) on the ready-made salt-coated filters.

Figure 27:
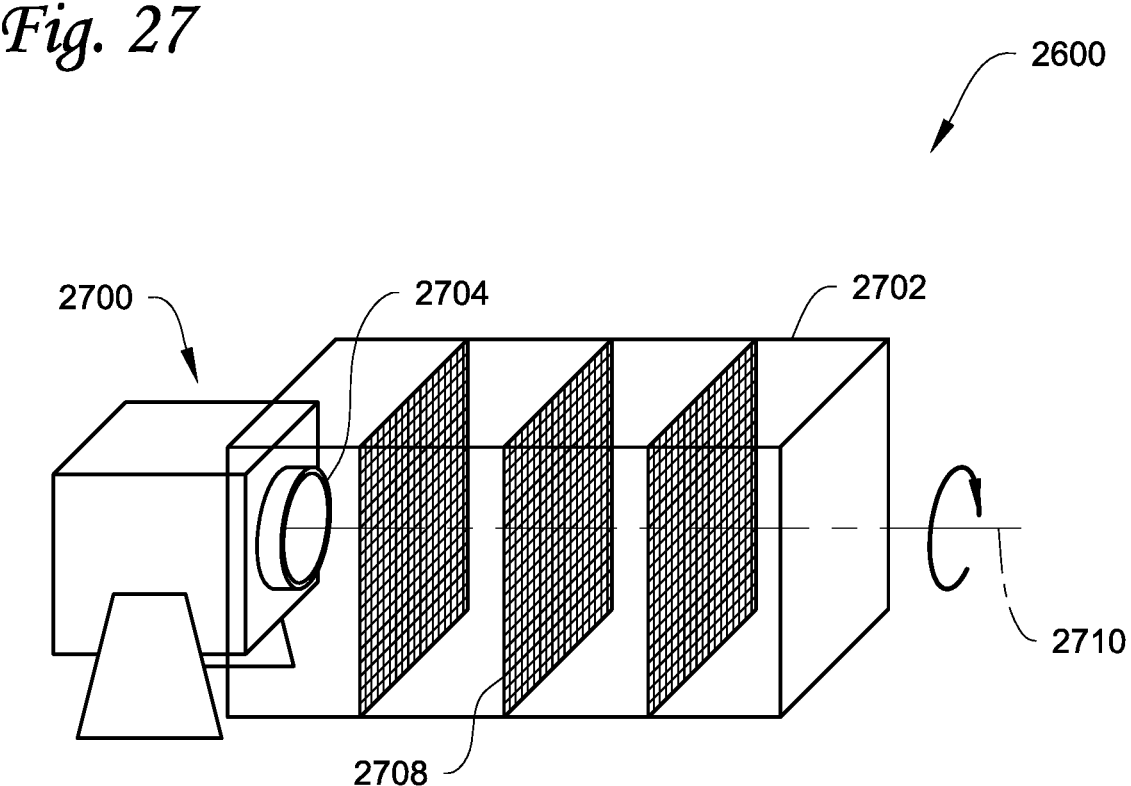
FIG. 27 shows a schematic illustration of a device for manufacturing a pathogen-deactivating filter material, according to an embodiment.
Figure 28:
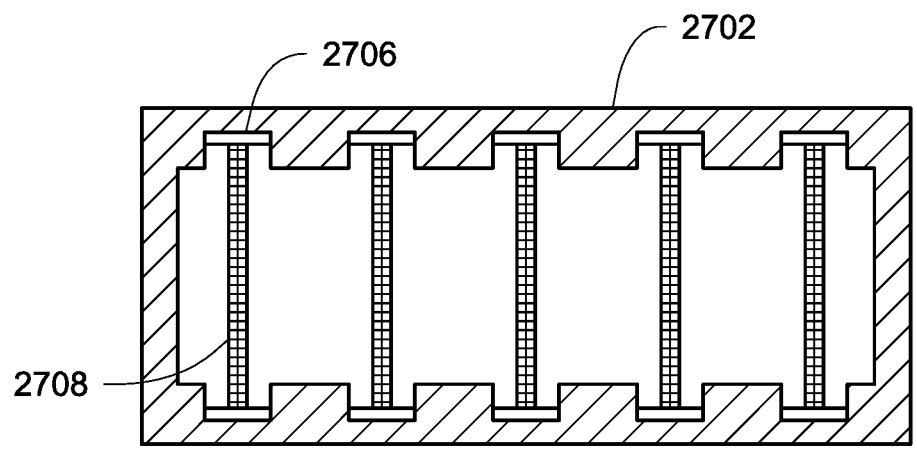
FIG. 28 shows a top view of a filter holder rack device shown in FIG. 27.

FIG. 27 shows a schematic illustration of a device 2700 for performing the drying step (G in FIG. 26), according to an embodiment. Further, FIG. 28 shows a top view of a filter holder rack 2702 shown in FIG. 27. The device 2700 is a rotator with a motor having a connecting portion 2704 for connecting to a holder rack 2702. The holder rack 2702 has an open top and an open bottom, and inner side surfaces 2706 configured to hold salt-coated filter materials 2708. When in operation, the device 2700 rotates the holder rack 2702 around an axis 2710 to induce uniform salt crystal formation on the filter (or the supporting member). The open top and open bottom can enhance drying rate compared to a completely closed bottom of a container. Since both top and bottom of the holder are open, the pre-wet or spray-coated supporting member are directly exposed to air, and this can accelerate the drying process. In an embodiment, the filter holder rack 2702 is configured to maximize water evaporation from the filter.

It is contemplated that different containers, holders, drying methods, and conditions can be used to control crystallization behavior of the salt (i.e. crystal size, orientation, morphology, etc.) in the pre-wet or spray coated supporting member so as to achieve a uniform salt crystal coating on the supporting member.

In some embodiments, the dried filter that is coated with salt crystals is directly used as a pathogen-deactivating filter. In some embodiments, the dried filter that is coated with salt crystals is disposed on one or more porous coating or membranes to obtain a pathogen-deactivating filter. In an embodiment, a pathogen-deactivating filter is obtained by sandwiching the dried filter coated with salt crystals with at least two hydrophobic coatings or membranes.

Figure 29:
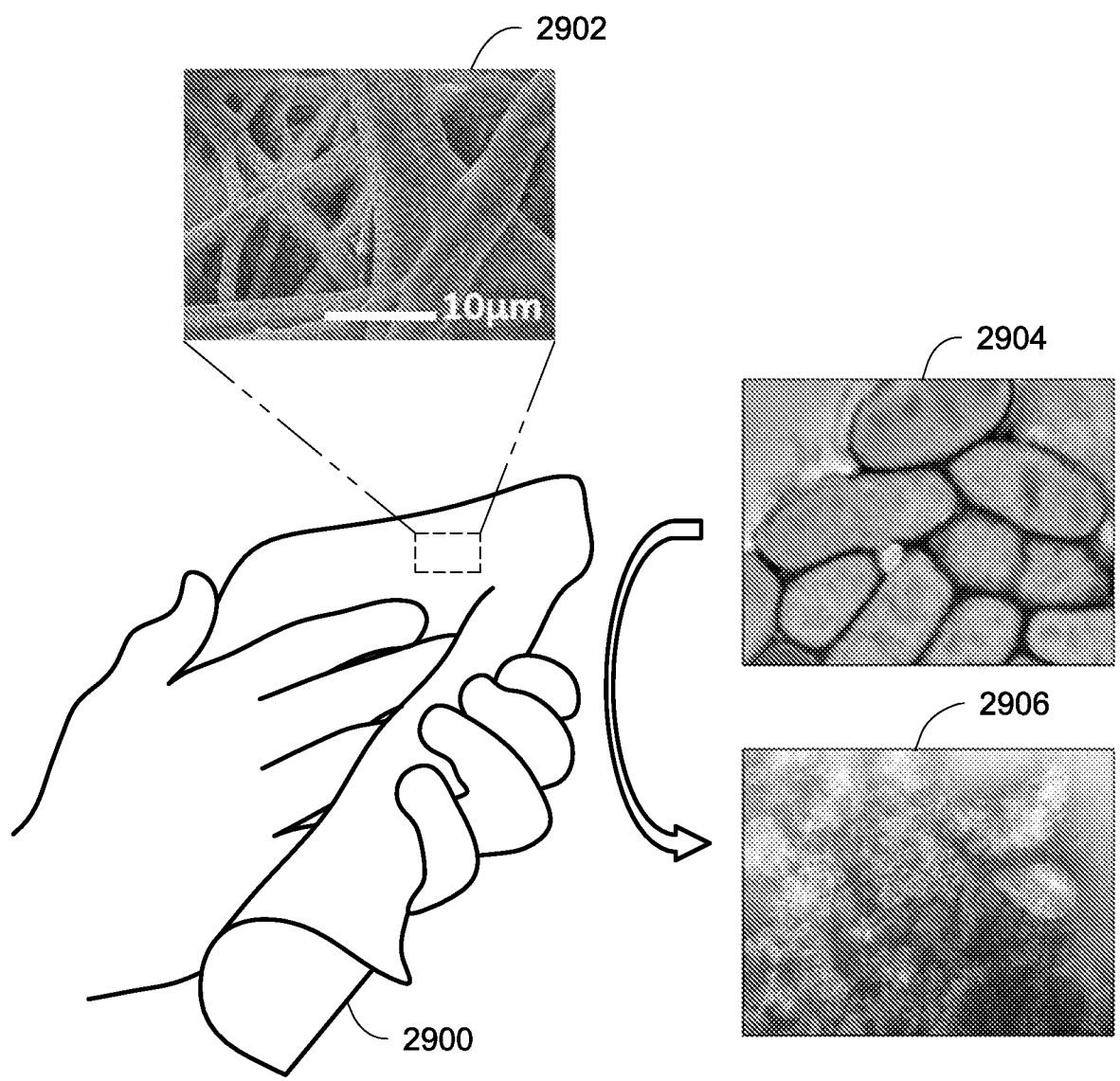
FIG. 29 shows a schematic illustration of a hand sanitizing device, according to an embodiment.

FIG. 29 shows a schematic illustration of a hand sanitizing device 2900, demonstrating deactivation of pathogens deposited on hands. The hand sanitizing device 2900 (e.g., a cloth) has a salt coating on a fiber surface as shown in the enhanced image 2902. The salt coating dissolves upon exposure to pathogens adsorbed on the hand surface with high moisture conditions and recrystallizes during drying, destroying the pathogens. At the same time, dissolution of the salt coating increases osmotic pressure and electrostatic interaction, resulting in further destabilization of pathogens. Thus, as shown in enhanced images 2904, 2906, pathogens (e.g., bacteria, virus, etc.) on a user's hand(s) is inactivated by the hand sanitizing device 2900. In some embodiments, the salt costing on the fiber surface of the device 2900 can deactivate pathogens adsorbed on a dry hand surface, by inducing denaturation of antigens and/or destruction of lipid envelopes upon contact with the pathogen through electrostatic interaction with the salt coating on the hand sanitizing device 2900.

In another embodiment, the salt-coated fabric can be used as sanitizing fabric products including a hand sanitizing device, decontamination garments, antibacterial wipes, hoods, gowns, apron, boots, and gloves for personal infection control measures.

It is contemplated that pathogenic aerosols and pathogens in high moisture environments are deactivated mainly by salt-recrystallization. However, pathogens adsorbed on dry surface or pathogens in dry environments can be deactivated by direct interaction with the salt surface through electrostatic interaction.

The terminology used in herein is intended to describe the particular embodiments and is not intended to be limiting. The use of the terms "a", "an", "the" and their plural forms to describe elements, components, ingredients or steps is not intended to foreclose additional elements, components, ingredients or steps. The terms "comprises," "comprising," and/or "comprised," when used in this specification and aspects, specify the presence of the stated elements, ingredients, components or steps, but do not preclude the presence or addition of one or more other elements, ingredients, components or steps.

The following lists various aspects of embodiments disclosed herein. It will be appreciated that any of the aspects may be combined with any other of the aspects.

Aspect 1. A material for deactivating a pathogenic aerosol, comprising:
 a supporting fibrous layer; and
 a salt crystal disposed on the supporting fibrous layer.

Aspect 2. The material of aspect 1, wherein the salt crystal includes an inorganic salt.

Aspect 3. The material of aspect 1, wherein the salt crystal includes one or more of sodium, potassium, chloride, magnesium, sulfate, ammonium, phosphate, glutamate, tartrate, and their ions.

Aspect 4. The material of aspects 1-3, wherein the salt crystal includes an organic salt.

Aspect 5. The material of aspect 4, wherein the organic salt includes one or more of phosphate, glutamate, tartrate, and their ions.

Aspect 6. The material of aspects 1-5, wherein the salt crystal is a coating layer which completely covers the supporting fibrous layer.

Aspect 7. The material of aspects 1-6, wherein the supporting fibrous layer includes a hydrophobic material.

Aspect 8. The material of aspects 1-7, wherein the supporting fibrous layer includes a hydrophilic material.

Aspect 9. An air filter device, comprising the material of any one or more of aspects 1-8.

Aspect 10. The air filter device of aspect 9, which is configured to be worn as a mask for covering a wearer's nose and mouth.

Aspect 11. The air filter device of aspect 9, which is configured to be a vehicle cabin air filter device, a furnace air filter device, or an air conditioner filter device.

Aspect 12. The air filter device of aspect 9, which is configured to be a respirator device.

Aspect 13. A method for manufacturing the material of aspects 1-8, comprising:
 coating the supporting fibrous layer with a salt-coating solution to obtain a salt coated fibrous layer; and
 drying the salt coated fibrous layer,
 wherein the salt-coating solution includes one or more of a salt, a surfactant, an additive, and an excipient.

Aspect 14. The method of aspect 13, wherein the salt-coating solution does not include a surfactant.

Aspect 15. The method of aspects 13 and 14, wherein the salt-coating solution does not include an additive.

Aspect 16. The method of aspects 13-15, wherein the salt-coating solution does not include an excipient.

Aspect 17. The method of aspects 13-16, wherein the coating step includes spray coating the supporting fibrous layer with the salt-coating solution.

Aspect 18. A method for deactivating an aerosol pathogen, comprising:
 adsorbing a pathogenic aerosol on to the air filter material of aspects 1-8;
 dissolving the salt on the air filter material with the pathogenic aerosol leading to an evaporation of water from the pathogenic aerosol; and
 recrystallizing the salt dissolved in the pathogenic aerosol and causing the pathogen to deactivate.

Aspect 19. A sanitary fabric device for deactivating a pathogenic aerosol, comprising:
 a supporting fibrous layer; and
 a salt crystal disposed on the supporting fibrous layer.

Aspect 20. The sanitary fabric device of aspect 19, wherein the salt crystal includes an inorganic salt.

Aspect 21. The sanitary fabric device of aspect 20, wherein the inorganic salt includes one or more of sodium, potassium, chloride, magnesium, sulfate, ammonium, and their ions.

Aspect 22. The sanitary fabric device of aspects 19-21, wherein the salt crystal includes an organic salt.

Aspect 23. The sanitary fabric device of aspect 22, wherein the organic salt includes one or more of phosphate, glutamate, tartrate, and their ions.

Aspect 24. The sanitary fabric device of aspects 19-23, wherein the salt crystal is a coating layer which completely covers the supporting fibrous layer.

Aspect 25. The sanitary fabric device of aspects 19-24, wherein the supporting fibrous layer includes a hydrophobic material.

Aspect 26. The sanitary fabric device of aspects 19-25, wherein the supporting fibrous layer includes a hydrophilic material.

Aspect 26. A method for manufacturing the sanitary fabric device of aspects 19-26, comprising:
 coating the supporting fibrous layer with a salt-coating solution to obtain a salt coated fibrous layer; and
 drying the salt coated fibrous layer,
 wherein the salt-coating solution includes one or more of a salt, a surfactant, an additive, and an excipient.

Aspect 27. The method of aspect 26, wherein the salt-coating solution does not include a surfactant.

Aspect 28. The method of aspects 26 and 27, wherein the salt-coating solution does not include an additive.

Aspect 29. The method of aspects 26-28, wherein the salt-coating solution does not include an excipient.

Aspect 30. A method for deactivating an aerosol pathogen, comprising:

adsorbing a pathogenic aerosol on to the sanitary fabric device of aspects 19-26;

dissolving the salt on the sanitary fabric device with the pathogenic aerosol leading to an evaporation of water from the pathogenic aerosol; and recrystallizing the salt dissolved in the pathogenic aerosol and causing the pathogen to deactivate.

What is claimed is:

1. A material for deactivating a pathogenic aerosol, comprising:

a supporting fibrous layer; and a salt crystal disposed on the supporting fibrous layer, wherein the salt crystal is a coating layer which partially or completely cover the supporting fibrous layer and the salt crystal includes one or more of sodium, potassium, chloride, magnesium, sulfate, ammonium, phosphate, glutamate, tartrate, and their ions, wherein the amount of the salt crystals disposed on the supporting fibrous layer is from 3.011 mg/cm$^2$ to 18.611 mg/cm$^2$, and the material has an air filtration efficiency of at least 5%.

2. The material of claim 1, wherein the supporting fibrous layer includes a hydrophobic material.

3. The material of claim 1, wherein the supporting fibrous layer includes a hydrophilic material.

4. The material of claim 1, wherein the salt crystal is configured to absorb a pathogenic aerosol, including the pathogen on to the supporting fibrous layer of claim 1.

5. An air filter device, comprising the material of claim 1.

6. The air filter device of claim 5, which is configured to be worn as a mask for covering a wearer's nose and mouth, wherein the mask comprises a facemask and ear straps connected to the facemask, the facemask is configured to cover the wearer's nose and mouth, and the ear straps are configured to wrap around the wearer's ears to support a position of the facemask.

7. The air filter device of claim 5, which is configured to be a respirator device, wherein the respirator device has a face piece, two filter cartridges disposed on the face piece, and a head strap connected to the face piece; the face piece is configured to cover a wearer's nose and mouth, and the head strap is configured to wrap around the wearer's head to support a position of the face piece.

8. The air filter device of claim 5, which is configured to be an air filter device, wherein the air filter device comprises a frame for retaining one or more layer(s) of filter material(s), and wherein the air filter device comprises a vehicle cabin air filter device, a furnace air filter device or an air conditioner filter device.

9. A sanitary device, comprising the material of claim 1.

10. The sanitary device of claim 9, which is configured to be used as a sanitizing fabric device, wherein the sanitizing fabric device comprises a salt coating on a fiber surface.

11. A decontamination garment, comprising the material of claim 1.

12. A method for manufacturing the material of claim 1, comprising:

coating the supporting fibrous layer with a salt-coating solution to obtain a salt coated fibrous layer, wherein the salt-coating solution is coated at a salt concentration sufficient to dissolve upon contact with the pathogenic aerosol, thereby increasing electrostatic interaction and osmotic pressure of the plurality of pathogens in the pathogenic aerosol and causing evaporation of water from the pathogenic aerosol, and the salt crystals are further configured to recrystallize the salt dissolved by the pathogenic aerosol and deactivates the plurality of pathogens from the pathogenic aerosol; and drying the salt coated fibrous layer, wherein the salt-coating solution includes one or more of a salt, a surfactant, an additive, and an excipient.

13. The method of claim 12, wherein the coating step includes spray coating the supporting fibrous layer with the salt-coating solution.

14. The material of claim 1, wherein a surface of the supporting fibrous layer coated with the salt crystal is configured to be hydrophilic.

* * * * *